US009163242B2

(12) United States Patent
Giangrande et al.

(10) Patent No.: US 9,163,242 B2
(45) Date of Patent: Oct. 20, 2015

(54) HER2 NUCLEIC ACID APTAMERS

(75) Inventors: Paloma H. Giangrande, Iowa City, IA (US); James O. McNamara, Iowa City, IA (US); Kristina W. Thiel, Iowa City, IA (US); William Thiel, Iowa City, IA (US); William M. Rockey, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 244 days.

(21) Appl. No.: 13/697,498

(22) PCT Filed: Apr. 27, 2011

(86) PCT No.: PCT/US2011/034169
§ 371 (c)(1),
(2), (4) Date: Feb. 4, 2013

(87) PCT Pub. No.: WO2011/142970
PCT Pub. Date: Nov. 17, 2011

(65) Prior Publication Data
US 2013/0129719 A1 May 23, 2013

Related U.S. Application Data

(60) Provisional application No. 61/334,947, filed on May 14, 2010.

(51) Int. Cl.
C07H 21/02 (2006.01)
C07H 21/04 (2006.01)
A61K 31/70 (2006.01)
C12N 15/115 (2010.01)
C12N 15/113 (2010.01)
A61K 31/7088 (2006.01)
A61K 39/395 (2006.01)
C12Q 1/68 (2006.01)

(52) U.S. Cl.
CPC .......... *C12N 15/115* (2013.01); *A61K 31/7088* (2013.01); *A61K 39/39558* (2013.01); *C12N 15/1135* (2013.01); *C12N 2310/14* (2013.01); *C12N 2310/16* (2013.01); *C12N 2310/3519* (2013.01); *C12N 2320/32* (2013.01)

(58) Field of Classification Search
None
See application file for complete search history.

(56) References Cited

U.S. PATENT DOCUMENTS 4,683,195 A 7/1987 Mullis et al.
4,683,202 A 7/1987 Mullis
4,800,159 A 1/1989 Mullis et al.
4,965,188 A 10/1990 Mullis et al.
5,837,834 A 11/1998 Pagratis et al.
6,124,449 A 9/2000 Gold et al.
2008/0214489 A1 9/2008 Keefe et al.

FOREIGN PATENT DOCUMENTS

WO WO 2007/143086 A2 12/2007

OTHER PUBLICATIONS

Aigner, "Gene siliencing through RNA interference (RNAi) in vivo: Strategies based on the direct application of siRNAs", *J. Biotechnology*, 124(1), 12-25 (2006).
Cerchia et al., "Cell-specific aptamers for targeted therapies", *Nucleic Acid and Peptide Aptamers: Methods and Protocols*, vol. 535, 59-78 (2009).
Chu et al., "Aptamer mediated siRNA delivery", *Nucleic Acids Res.*, 34(10), e73, 6 pages (2006).
Dassie et al., "Systemic administration of optimized aptamer-siRNA chimeras promotes regression of PSMA-expressing tumors", *Nat. Biotechnol.*, 27(9), 839-849 (2009).
Heidel et al., "Administration in non-human primates of escalating intravenous doses of targeted nanoparticles containing ribonucleotide reductase subunit M2 siRNA", *Proc. Natl. Acad. Sci*, 104(14), 5715-5721 (2007).
Hernandez et al., "Methods for Evaluating Cell-Specific, Cell-Internalizing RNA Aptamers", *Pharmaceuticals*, 6, 295-319 (2013).
Howard et al., "RNA Interference in Vitro and in Vivo Using a Chitosan/siRNA Nanoparticle System", *Mol. Ther.*, 14(4), 476-484 (2006).
Hu-Lieskovan et al., "Sequence-Specific Knockdown of EWS-FLI1 by Targeted, Nonviral Delivery of Small Interfering RNA Inhibits Tumor Growth in a Murine Model of Metastatic Ewing's Sarcoma", *Cancer Res.* 65(19), 8984-8992 (2005).
Jonathan, "SELEX: Part 3, A Bit About the Math", [Retrieved from the Internet Oct. 26, 2011: http://workingthebench.blogspot.com/2008/07/selex-part-3-bit-about-math.html], 2 pages (2008).
Kamada et al., "*bcl-2* Deficiency in Mice Leads to Pleiotropic Abnormalities: Accelerated Lymphoid Cell Death in Thymus and Spleen, Polycystic Kidney, Hair Hypopigmentation, and Distorted Small Intestine", *Cancer Research*, 55, 354-359 (1995).
Kang et al., "Isolation of RNA Aptamers Targeting HER-2-overexpressing Breast Cancer Cells Using Cell-SELEX", *Bull. Korean Chem. Soc.*, vol. 30, No. 8, 1827-1831 (2009).
Kim et al., "Functional interaction between mouse erbB3 and wild-type rat c-*neu* in transgenic mouse mammary tumor cells", *Breast Cancer Research*, 7, R708-R718 (2005).
Kumar et al., "Transvascular delivery of small interfering RNA to the central nervous system", *Nature*, 448, 39-43 (2007).

(Continued)

*Primary Examiner* — Sean McGarry
(74) *Attorney, Agent, or Firm* — Viksnins Harris & Padys PLLP

(57) ABSTRACT

The present invention relates to optimized HER2 aptamers and methods of using these aptamers.

19 Claims, 19 Drawing Sheets

(56) References Cited

OTHER PUBLICATIONS

Kunz et al., "Peptide Aptamers with Binding Specificity for the Intracellular Domain of the ErbB2 Receptor Interfere with AKT Signaling and Sensitize Breast Cancer Cells to Taxol", *Mol. Cancer Res.*, 4(12), 983-998 (2006).

Liu et al., "Low-Dose Dietary Phytoestrogen Abrogates Tamoxifen-Associated Mammary Tumor Prevention", *Cancer Res*, 65 (3), 879-886 (2005).

Liu et al., "Bos taurus clone CH240-196A23, Working Draft Sequence, 13 unordered pieces", GenBank: AC166790.3, [Retrieved from the internet Feb. 9, 2012:url:http://www.ncbi.nlm.nih.gov/nuccore/ac166790; nucleotides 203493-203511, 51 pages (2008).

Lollini et al., "Down Regulation of Major Histocompatibility Complex Class I Expression in Mammary Carcinoma of HER-2/neu Transgenic Mice", *Int. J. Cancer*, 77, 937-941 (1998).

McNamara et al., "Cell type-specific delivery of siRNAs with aptamer-siRNA chimeras", *Nat. Biotechnol.* 24(8), 1005-1015 (2006).

McNamara II et al, "Multivalent 4-1BB binding aptamers costimulate CD8+ T cells and inhibit tumor growth in mice", *Journal of Clinical Investigation*, vol. 118 (1), 376-786 (2008).

Meade et al., "Exogenous siRNA delivery using peptide transduction domains/cell penetrating peptides", *Adv. Drug Delivery Rev.*, 59(2-3), 134-140 (2007).

Nanni et al., "p185neu Protein is Required for Tumor and Anchorage-Independent Growth, not for Cell Proliferation of Transgenic Mammary Carcinoma", *Int. J. Cancer*, 87, 186-194 (2000).

Oakes et al., "Proapoptotic BAX and BAK regulate the type 1 inositol trisphosphate receptor and calcium leak from the endoplasmic reticulum", *PNAS*, vol. 102 (1), 105-110 (2005).

Patent Cooperation Treaty, International Searching Authority, Search Report and Written Opinion for PCT/US11/34169, 14 pages, Mar. 9, 2012.

Peer et al., "Selective gene silencing in activated leukocytes by targeting siRNAs to the integrin lymphocyte function-associated antigen-1", *Proc. Natl Acad. Sci.*, 104(10), 4095-4100 (2007).

Pille et al., "Intravenous Delivery of Anti-RhoA Small Interfering RNA Loaded in Nanoparticles of Chitosan in Mice: Safety and Efficacy in Xenografted Aggressive Breast Cancer", *Hum. Gene Ther.* 17(10), 1019-1026 (2006).

Rozema et al., "Dynamic PolyConjugates for targeted in vivo delivery of siRNA to hepatocytes", *Proc. Natl. Acad. Sci.* 104(32), 12982-12987 (2007).

Shaw et al., "Boranophosphate siRNA-aptamer chimeras for tumor-specific downregulation of cancer receptors and modulators", *Nucleic Acids Symp Ser*, 52, 655-656 (2008).

Song et al., "Antibody mediated in vivo delivery of small interfering RNAs via cell-surface receptors", *Nat. Biotechnol.*, 23(6), 709-717 (2005).

Takei et al., "A Small Interfering RNA Targeting Vascular Endothelial Growth Factor as Cancer Therapeutics", *Cancer Res.*, 64(10), 3365-3370 (2004).

Takeshita et al., "Therapeutic potential of RNA interference against cancer", *Cancer Sci*, 97(8), 689-696 (2006).

Thiel et al., "Therapeutic applications of DNA and RNA aptamers", *Oligonucleotides*, 19(2), 209-222 (2009).

Thiel, K.W., "Delivery of chemo-sensitizing siRNAs to HER2-positive breast cancer cells using RNA aptamers", Abstract No. 150276, American Society of Gene & Cell Therapy 13th Annual Meeting, 2 pages (2010).

Thiel, W. H., "Methods for isolating cell-internalizing RNA aptamers for targeted siRNA delivery" Abstract No. 663, ASGT (2010).

Thiel et al., "Delivery of chemo-sensitizing siRNAs to HER2+-breast cancer cells using RNA aptamers", *Nucleic Acids Research*, 1-19 (2012).

Wullner et al., "Cell-specific induction of apoptosis by rationally designed bivalent aptamer-siRNA transcripts silencing eukaryotic elongation factor 2", *Curr. Cancer Drug Targets*, 8(7), 554-565 (2008).

Zhou et al., "Novel dual inhibitory function aptamer-siRNA delivery system for HIV-1 therapy", *Mol. Ther.*, 16(8), 1481-1489 (2008).

Zhou et al., "The therapeutic potential of cell-internalizing aptamers", *Curr. Top Med. Chem.*, 9(12), 1144-1157 (2009).

Zhou et al., "Selection, characterization and application of new RNA HIV gp 120 aptamers for facile delivery of Dicer substrate siRNAs into HIV infected cells", *Nucleic Acids Res.*, 37(9), 3094-3109 (2009).

C

HER2 NUCLEIC ACID APTAMERS

RELATED APPLICATION

This application is the U.S. National Phase application of Patent Cooperation Treaty Application Number PCT/US2011/034169, filed on Apr. 27, 2011, which claims priority U.S. Provisional Patent Application No. 61/334,947, filed May 14, 2010, the entirety of which are incorporated herein by reference.

GOVERNMENT FUNDING

This invention was made with government support under Grant Number R01 1R01CA138503-01 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on May 13, 2010, is named 17023111.txt and is 12,001 bytes in size.

BACKGROUND

RNA interference (RNAi) is a cellular mechanism by which 21-23 nucleotide RNA duplexes trigger the degradation of cognate mRNAs. Researchers have been pursuing potential therapeutic applications of RNAi once it was demonstrated that exogenous, short interfering RNAs (siRNAs) can silence gene expression via this pathway in mammalian cells. RNAi is attractive for therapeutics because of its stringent target gene specificity, the relatively low immunogenicity of siRNAs, and the simplicity of design and testing of siRNAs.

Double-stranded RNA (dsRNA) can induce sequence-specific posttranscriptional gene silencing in many organisms by a process known as RNA interference (RNAi). However, in mammalian cells, dsRNA that is 30 base pairs or longer can induce sequence-nonspecific responses that trigger a shutdown of protein synthesis. RNA fragments are the sequence-specific mediators of RNAi. Interference of gene expression by these RNA interference (RNAi) molecules is now recognized as a naturally occurring strategy for silencing genes in the cells of many organisms.

One technical hurdle for RNAi-based clinical applications that still remains is the delivery of siRNAs across the plasma membrane of cells in vivo. A number of solutions for this problem have been described. However, most of the approaches described to date have the disadvantage of delivering siRNAs to cells non-specifically, without regard to the cell type.

For in vivo use, the therapeutic siRNA reagents need to target particular cell types (e.g., cancer cells), thereby limiting side-effects that result from non-specific delivery as well as reducing the quantity of siRNA necessary for treatment.

SUMMARY

Accordingly, in certain embodiments, the present invention provides an aptamer molecule not more than 55 nucleotides in length comprising the nucleic acid sequence 5'-GGGAGGACGAUGCGG-R$^1$-CAGACGACUCGCCCGA-3' (SEQ ID NO: 45), wherein R$^1$ is (n)$_x$ where each n represents any nucleotide, and wherein x is an integer from 19 to 21. In certain embodiments, R$^1$ is

```
                              (A-consensus, SEQ ID NO: 7)
       GACUGUAYGGGGCUCUGUG, (D-consensus, SEQ ID NO: 11)
       AUGUAUGUUGGGAGCCACGC, (B-consensus, SEQ ID NO: 15)
       UCUGUUGUGCUUGAUAUGCCC, (C-consensus, SEQ ID NO: 21)
       CUGUCUWMGCUUCUACUGCCG, (E-consensus, SEQ ID NO: 24)
       UCCUGUCGUYUGKUCSKCCC.
```

The present invention, in certain embodiments, provides a complex comprising the an aptamer molecule not more than 55 nucleotides in length comprising the nucleic acid sequence 5'-GGGAGGACGAUGCGG-R$^1$-CAGACGACUCGC-CCGA-3' (SEQ ID NO: 45), wherein R$^1$ is (n)$_x$ where each n represents any nucleotide, and wherein x is an integer from 19 to 21 linked to a therapeutic or diagnostic molecule. In certain embodiments, the therapeutic molecule is a siRNA molecule. In certain embodiments, the siRNA has a guide strand and a passenger strand, and wherein the guide strand is linked to the nucleic acid molecule.

In certain embodiments, the nucleic acid molecule further includes a PEG molecule. In certain embodiments, the PEG molecule has an average molecular weight of about 10 to 100 kDa in size. In certain embodiments, the PEG molecule has an average molecular weight of about 10 to 40 kDa in size. In certain embodiments, the PEG molecule is PEG-20.

In certain embodiments, "linked" includes directly linking (covalently or non-covalently binding) the nucleic acid molecule of the invention (e.g., an aptamer) to a therapeutic or diagnostic molecule.

In certain embodiments, "linked" includes linking the nucleic acid molecule of the invention (e.g., an aptamer) to a therapeutic or diagnostic molecule using a linker, e.g., a nucleotide linker, e.g., the nucleotide sequence "AA" or "TT" or "UU".

In certain embodiments, the nucleic acid molecule of the invention (e.g., an aptamer) is linked to a diagnostic molecule.

In certain embodiments, the nucleic acid molecule of the invention (e.g., an aptamer) is linked to a therapeutic molecule.

In certain embodiments, the therapeutic molecule is an RNAi molecule, such as a siRNA molecule, e.g., a siRNA molecule targeted to Bcl-2. While certain exemplary siRNA sequences have been utilized herein, the invention is also directed to the use of other siRNA sequences, for example, siRNA sequences that target genes involved in cancer.

In certain embodiments, the therapeutic molecule is a nucleic acid molecule duplex.

In certain embodiments, the therapeutic molecule is a microRNA (miRNA).

Certain embodiments of the invention provide a nucleic acid molecule encoding a molecule, duplex or conjugate of the invention.

Certain embodiments of the invention provide an expression cassette including at least one nucleic acid molecule of the invention.

In certain embodiments, the expression cassette further includes a promoter, such as a regulatable promoter or a constitutive promoter. Examples of suitable promoters include a CMV, RSV, pol II or pol III promoter. The expression cassette may further contain a polyadenylation signal (such as a synthetic minimal polyadenylation signal) and/or a marker gene. Examples of marker genes include visual markers such as GFP, or functional markers, such as antibiotic resistance genes.

Certain embodiments of the invention provide a vector, e.g., a viral vector, including at least one (e.g., 1 or 2) expression cassette of the invention. Examples of appropriate vectors include adenoviral, lentiviral, adeno-associated viral (AAV), poliovirus, HSV, or murine Maloney-based viral vectors. In one embodiment, the vector is an adenoviral vector. In certain embodiments, a vector may contain two expression cassettes, a first expression cassette containing a nucleic acid encoding the first strand of the RNA duplex and a second expression cassette containing a nucleic acid encoding the second strand of the RNA duplex.

Certain embodiments of the invention provide an isolated or non-human cell including the HER2 receptor and a molecule, duplex or conjugate of the invention.

Certain embodiments of the invention provide methods for delivering a therapeutic or diagnostic molecule to a cell having a HER2 receptor, including contacting the cell with a conjugate of the invention.

Certain embodiments of the invention provide a pharmaceutical composition including a molecule, duplex or conjugate of the invention and a pharmaceutically acceptable carrier.

Certain embodiments of the invention provide a method for treating a patient having cancer including administering a molecule, duplex or conjugate of the invention to the patient.

Certain embodiments of the invention provide a method for determining whether a patient has cancer (i.e., diagnosing a patient) including administering a conjugate of the invention to the patient and determining whether the patient has cancer. For example, because certain conjugates of the invention are targeted to the HER2 receptor and include a diagnostic molecule, detection of a relatively higher level of the conjugate can be used to diagnose a patient as having breast cancer.

Certain embodiments of the invention provide a molecule, duplex or conjugate of the invention for use in therapy.

Certain embodiments of the invention provide the use of a molecule, duplex or conjugate of the invention for treating cancer.

Certain embodiments of the invention provide a molecule, duplex or conjugate of the invention for use in the prophylactic or therapeutic treatment of cancer. In certain embodiments, the cancer is a solid sarcoma or carcinoma. In certain embodiments, the cancer is breast cancer.

The present invention relates to a specific delivery of siRNAs and one that, at least in one embodiment, only uses properties of RNA. The delivery method of the instant invention exploits the structural potential of nucleic acids (e.g., RNA) to target siRNAs to a particular cell-surface receptor and thus to a specific cell type. In one embodiment, the invention provides a method and compositions to specifically deliver nucleic acids that comprise both a targeting moiety (e.g., an aptamer) and an RNA-silencing moiety (e.g., an siRNA) that is recognized and processed by Dicer in a manner similar to the processing of microRNAs. Aptamers and siRNAs have low immunogenicity. They can easily be synthesized in large quantities at a relatively low cost and are amendable to a variety of chemical modifications that confer both resistance to degradation and improved pharmacokinetics in vivo. The smaller size of aptamers compared with that of antibodies (<15 kDa versus 150 kDa) facilitates their in vivo delivery by promoting better tissue penetration.

In certain embodiments of the invention, RNAi molecules are employed to inhibit expression of a target gene. By "inhibit expression" is meant to reduce, diminish or suppress expression of a target gene. Expression of a target gene may be inhibited via "gene silencing." Gene silencing refers to the suppression of gene expression, e.g., transgene, heterologous gene and/or endogenous gene expression, which may be mediated through processes that affect transcription and/or through processes that affect post-transcriptional mechanisms. In some embodiments, gene silencing occurs when an RNAi molecule initiates the degradation of the mRNA transcribed from a gene of interest in a sequence-specific manner via RNA interference, thereby preventing translation of the gene's product.

As used herein the term "encoded by" is used in a broad sense, similar to the term "comprising" in patent terminology. For example, the statement "the first strand of RNA is encoded by SEQ ID NO:1" means that the first strand of RNA sequence corresponds to the RNA sequence transcribed from the DNA sequence indicated in SEQ ID NO:1, but may also contain additional nucleotides at either the 3' end or at the 5' end of the RNA molecule.

The reference to siRNAs herein is meant to include short hairpin RNAs (shRNAs) and other small RNAs that can or are capable of modulating the expression of a target gene, for example via RNA interference. Such small RNAs include without limitation, shRNAs and miroRNAs (miRNAs).

The two strands of RNA in the siRNA may be completely complementary, or one or the other of the strands may have an "overhang region" (i.e., a portion of the RNA that does not bind with the second strand). Such an overhang region may be from 1 to 10 nucleotides in length.

The present invention provides a method of reducing Bcl-2 accumulation in a mammal in need thereof, e.g., by introducing the vector encoding a miRNA in an amount sufficient to suppress accumulation of Bcl-2. The Bcl-2 protein can be inhibited by at least 10%, 20%, 30%, 40%, 50%, 60%, 70%, 80%, 90%, 95%, or 99%.

This invention relates to compounds, compositions, and methods useful for inhibiting Bcl-2 gene expression using short interfering nucleic acid (siRNA) molecules. This invention also relates to compounds, compositions, and methods useful for modulating the expression and activity of Bcl-2 by RNA interference (RNAi) using small nucleic acid molecules. In particular, the instant invention features small nucleic acid molecules, such as short interfering nucleic acid (siNA), short interfering RNA (siRNA), double-stranded RNA (dsRNA), micro-RNA (miRNA), and short hairpin RNA (shRNA) molecules and methods used to modulate the expression of Bcl-2 genes. A siRNA of the instant invention can be chemically synthesized, expressed from a vector or enzymatically synthesized.

The present invention provides a mammalian cell containing an isolated first strand of RNA of 15 to 30 nucleotides in length, and an isolated second strand of RNA of 15 to 30 nucleotides in length, wherein the first strand contains a sequence that is complementary to for example at least 15 nucleotides of RNA encoded by a targeted gene of interest (for example the Bcl-2 gene), wherein for example at least 12 nucleotides of the first and second strands are complementary to each other and form a small interfering RNA (siRNA) duplex for example under physiological conditions, and wherein the siRNA silences (for example via RNA interference) only one allele of the targeted gene (for example the mutant allele of Bcl-2 gene) in the cell. The duplex of the siRNA may be between 15 and 30 base pairs in length. The two strands of RNA in the siRNA may be completely complementary, or one or the other of the strands may have an "overhang region" or a "bulge region" (i.e., a portion of the RNA that does not bind with the second strand or where a portion of the RNA sequence is not complementary to the sequence of the other strand). These overhangs may be at the 3' end or at the 5' region, or at both 3' and 5' ends. Such overhang regions may be from 1 to 10 (e.g., 1, 2, 3, 4, 5, 6, 7, 8, 9, 10) or more nucleotides in length. The bulge regions may be at the ends or in the internal regions of the siRNA duplex. Such bulge regions may be from 1-5 (e.g., 1, 2, 3, 4, 5) or more nucleotides long. Such bulge regions may be the bulge regions characteristic of miRNAs.

In the present invention, an expression cassette may contain a nucleic acid encoding at least one strand of the RNA duplex described above. Such an expression cassette may further contain a promoter. The expression cassette may be contained in a vector. These cassettes and vectors may be contained in a cell, such as a mammalian cell. A non-human mammal may contain the cassette or vector. The vector may contain two expression cassettes, the first expression cassette containing a nucleic acid encoding the first strand of the RNA duplex, and a second expression cassette containing a nucleic acid encoding the second strand of the RNA duplex.

The present invention further provides a method of substantially silencing a target gene of interest or targeted allele for the gene of interest in order to provide a therapeutic effect. As used herein the term "substantially silencing" or "substantially silenced" refers to decreasing, reducing, or inhibiting the expression of the target gene or target allele by at least about 5%, 10%, 15%, 20%, 25%, 30%, 35%, 40%, 45%, 50%, 55%, 60%, 65%, 70%, 75%, 80%, 85% to 100%. As used herein the term "therapeutic effect" refers to a change in the associated abnormalities of the disease state, including pathological and behavioral deficits; a change in the time to progression of the disease state; a reduction, lessening, or alteration of a symptom of the disease; or an improvement in the quality of life of the person afflicted with the disease. Therapeutic effect can be measured quantitatively by a physician or qualitatively by a patient afflicted with the disease state targeted by the siRNA. In certain embodiments wherein both the mutant and wild type allele are substantially silenced, the term therapeutic effect defines a condition in which silencing of the wild type allele's expression does not have a deleterious or harmful effect on normal functions such that the patient would not have a therapeutic effect.

In one embodiment, the expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is flanked (5' and 3') with functional sequences, such as sequences encoding an aptamer and/or siRNA.

In one embodiment, the selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from nonviral genes, such as the murine metallothionein gene, will also find use herein. Such promoter sequences are commercially available from, e.g., Stratagene® (San Diego, Calif.).

In one embodiment, pharmaceutical compositions will comprise sufficient genetic material to produce a therapeutically effective amount of the siRNA of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

In certain embodiments, a combination of an aptamer molecule not more than 55 nucleotides in length comprising the nucleic acid sequence 5'-GGGAGGACGAUGCGG-$R^1$-CA-GACGACUCGCCCGA-3' (SEQ ID NO: 45), wherein $R^1$ is $(n)_x$ where each n represents any nucleotide, and wherein x is an integer from 19 to 21 linked to a therapeutic or diagnostic molecule and Herceptin are administered.

| SEQ ID NO | Identifier |
|---|---|
| SEQ ID NO: 1 | A1 |
| SEQ ID NO: 2 | A2 |
| SEQ ID NO: 3 | A3 |
| SEQ ID NO: 4 | A4 |
| SEQ ID NO: 5 | A5 |
| SEQ ID NO: 6 | A6 |
| SEQ ID NO: 7 | A consensus |
| SEQ ID NO: 8 | D1 |
| SEQ ID NO: 9 | D2 |
| SEQ ID NO: 10 | D3 |
| SEQ ID NO: 11 | D consensus |
| SEQ ID NO: 12 | B1 |
| SEQ ID NO: 13 | B2 |
| SEQ ID NO: 14 | B3 |
| SEQ ID NO: 15 | B consensus |
| SEQ ID NO: 16 | C1 |
| SEQ ID NO: 17 | C2 |
| SEQ ID NO: 18 | C3 |
| SEQ ID NO: 19 | C4 |
| SEQ ID NO: 20 | C5 |
| SEQ ID NO: 21 | C consensus |
| SEQ ID NO: 22 | E1 |
| SEQ ID NO: 23 | E2 |
| SEQ ID NO: 24 | E consensus |

(B) Consensus sequences for each family were used to generate predicted secondary structures using RNAStructure. Interchangeable nucleotides in the consensus sequences for families A, C, and E are highlighted in red. These nucleotides do not change the overall predicted secondary structure. The consensus sequence for family B generated three distinct predicted secondary structures. The sequences are as follows:

| SEQ ID NO | Identifier |
|---|---|
| SEQ ID NO: 25 | Aptamer A |
| SEQ ID NO: 26 | Aptamer B |
| SEQ ID NO: 27 | Aptamer C |
| SEQ ID NO: 28 | Aptamer D |
| SEQ ID NO: 29 | Aptamer E |

Figure 1:
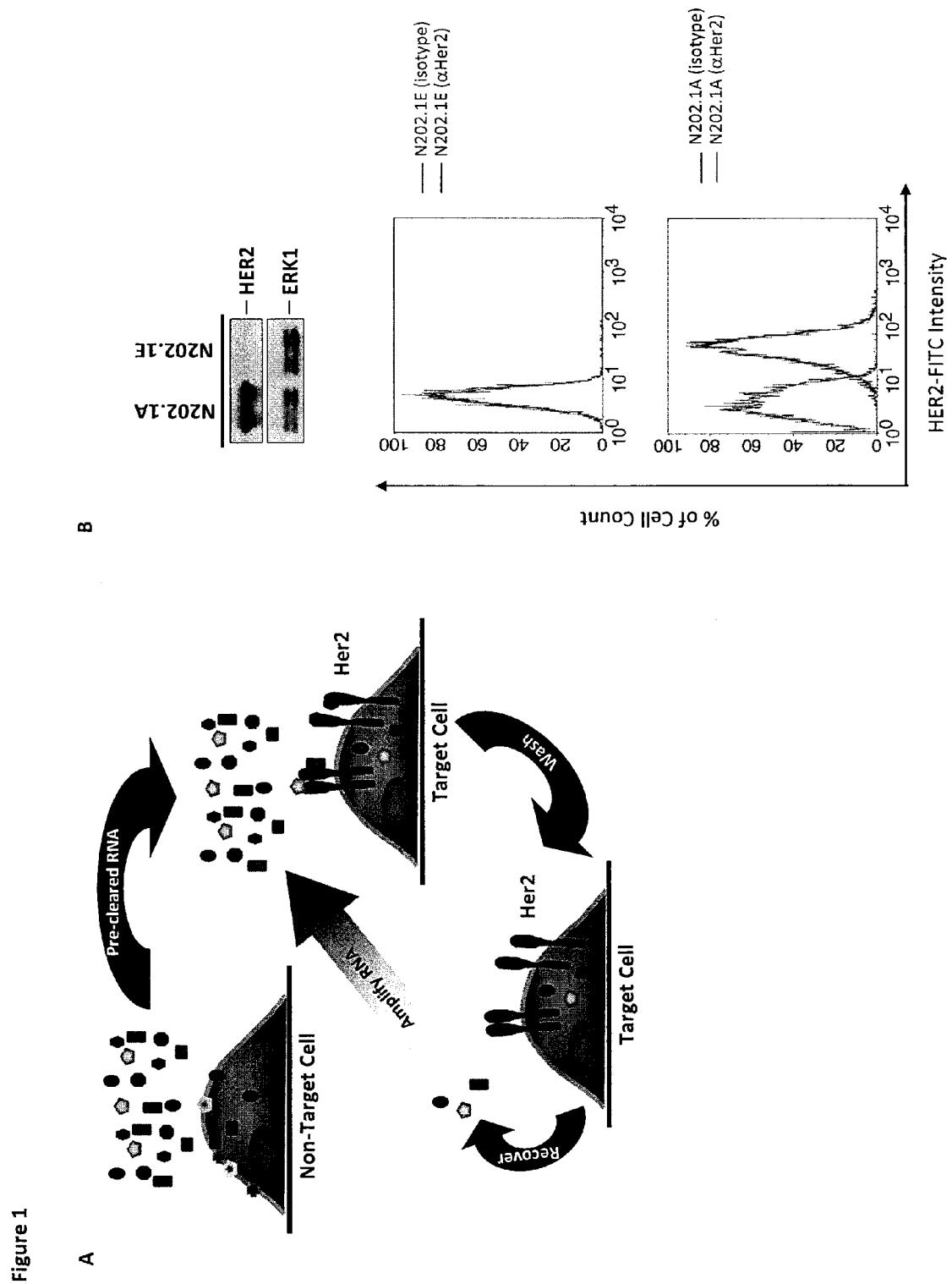
FIG. 1A-1D: Cell-Internalization SELEX (systematic evolution of ligands by exponential enrichment). (A) Schematic of the methodology used to isolate internalizing aptamers specific for HER2-positive target cells. (B) Equal amount of lysates from N202.1A and N202.1E cell were blotted for HER2 protein (upper panel). N202.1E and N202.1A cells were derived from tumors excised from the mouse mammary tumor virus (MMTV)-neu transgenic mice (Lollini et al., Down regulation of Major Histocompatibility Complex class I expression in mammary carcinoma of HER-2/neu transgenic mice. *Int. J. Cancer.* 1998. 77: 937-941; Nanni et al., p185 protein is required for tumor and anchorage-independent growth, not for cell proliferation of transgenic mammary carcinoma. *Int. J. Cancer.* 2000. 87: 186-194). ERK1 was used as a loading control. Cell surface expression of HER2 on N202.1A but not N202.1E cells was confirmed by flow cytometry using non-permeablized cells stained with either isotype control antibody or HER2-FITC (lower panels). Black: N202.1E isotype control; grey: N202.1A isotype control; blue: N202.1E+anti-HER2-FITC; green: N202.1A+ anti-HER2-FITC. (C) After nine rounds of cell-internalization SELEX using N202.1A as target cells and N202.1E as non-target cells, pools of aptamers from each round were analyzed using quantitative RT-PCR (qRT-PCR). Samples were normalized to an internal reference (M12-23 Sell aptamer (McNamara et al., Multivalent 4-1BB binding aptamers costimulate CD8+ T cells and inhibit tumor growth in mice. *J Clin Invest.* 2008. 118(1):376-86)). (D) Aptamer pools from rounds 0, 2, 4, 6, 8 and 9 were sequenced by 454-deep sequencing. Enrichment at each round was determined by the indicated formula.
Figure 1:
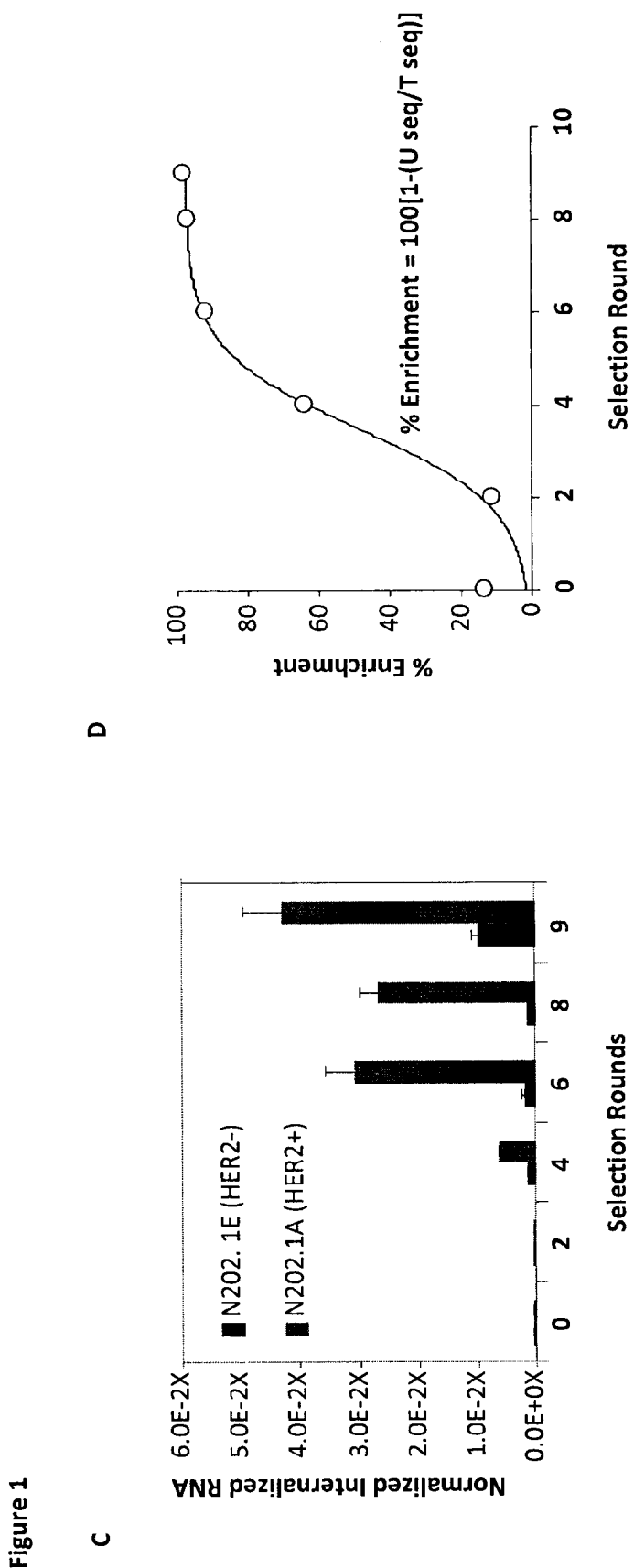

(C) Single aptamers were evaluated for internalization into HER2 negative (N202.1E) and HER2-positive (N202.1A) cells by qRT-PCR as in FIG. 1C. (D) Internalization into 78717 (HER2−) and 85819 (HER2+) mammary carcinoma cells (Kim et al., Functional Interaction between mouse erbB3 and wild type rat c-neu in transgenic mouse mammary tumor cells. *Breast Cancer Res* 2005; 7: R708-R718; Liu et al., Low dose dietary phytoestrogen abrogates tamoxifen associated mammary tumor prevention. *Cancer Res* 2005; 65: 879-86) was evaluated by qRT-PCR. (E) FAM-G aptamers were used to measure internalization into N202.1E (HER2−) and N202.1A (HEr2+) cells by flow cytometry.

Figure 3:
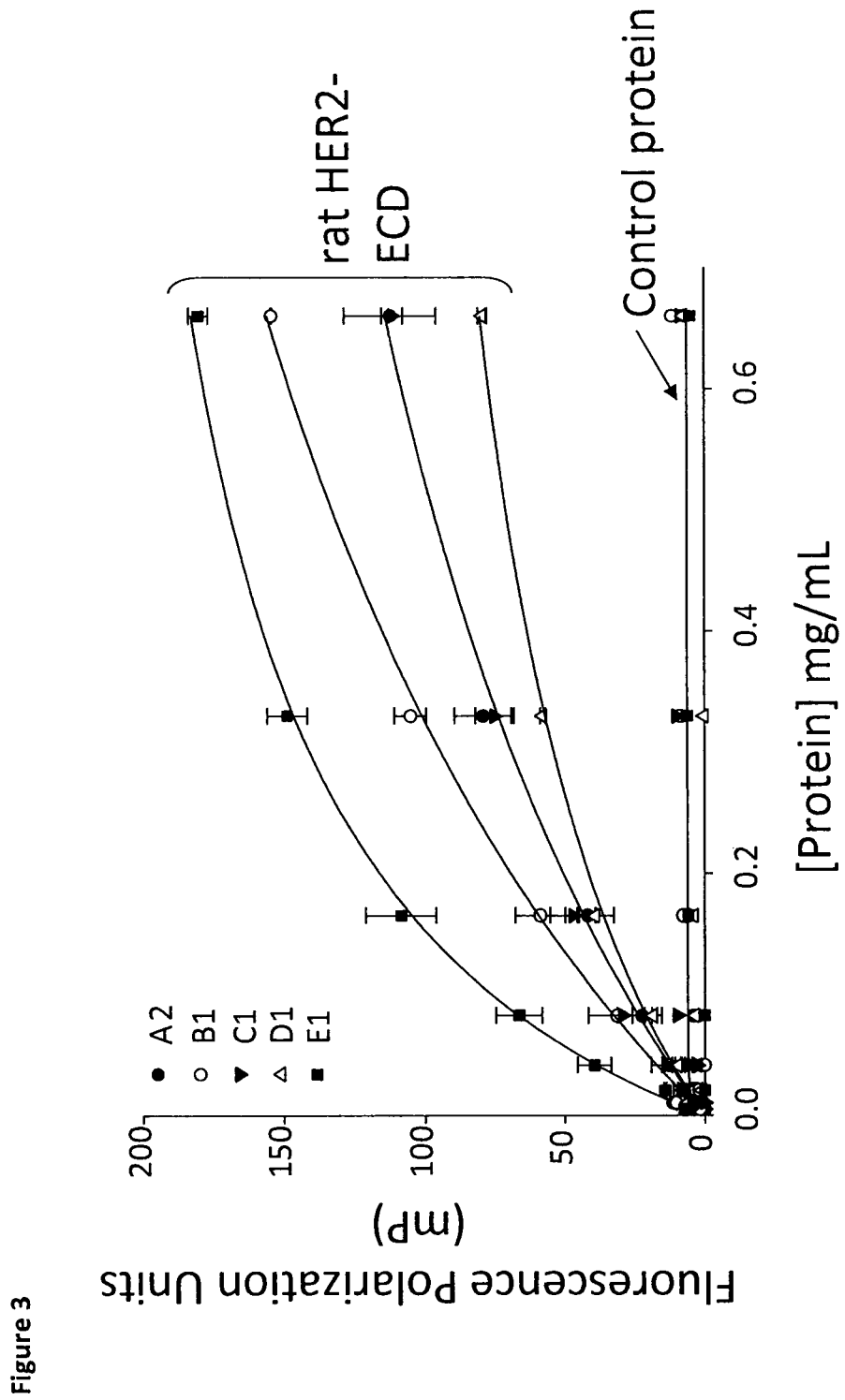

FIG. 3. Binding of HER2-aptamers to recombinant HER2-ECD protein. RNA aptamers labeled with FAM at the 5' end were incubated with recombinant rat HER2-ECD protein in increasing concentrations up to 1 µM at room temperature for 30 minutes in 100 µL reaction volumes. A non-target protein (glyoxylase) is used as a negative control in these assays (Control protein). The binding reaction is performed in the buffer in which the selection was performed. Fluorescence polarization (FP) values for each RNA concentration are read using an Analyst HT plate reader by LJL Biosystems. FP is given by $P=(V-H)/(V+H)$, where V is the vertical component of polarized light, and H is the horizontal component of polarized light. Values of polarization range from 0 to 500 mP, with 0 mP being no binding of the RNA and 500 mP representing maximal binding. The curve is fit with a one-site binding model using non-linear regression software. This confirms the binding of the HER2 aptamers to mouse HER2 using Fluorescence Polarization. No binding was observed to a control, non-target protein (his-tagged glyoxylase). This experiment was done several times and was reproducible.

Figure 4:
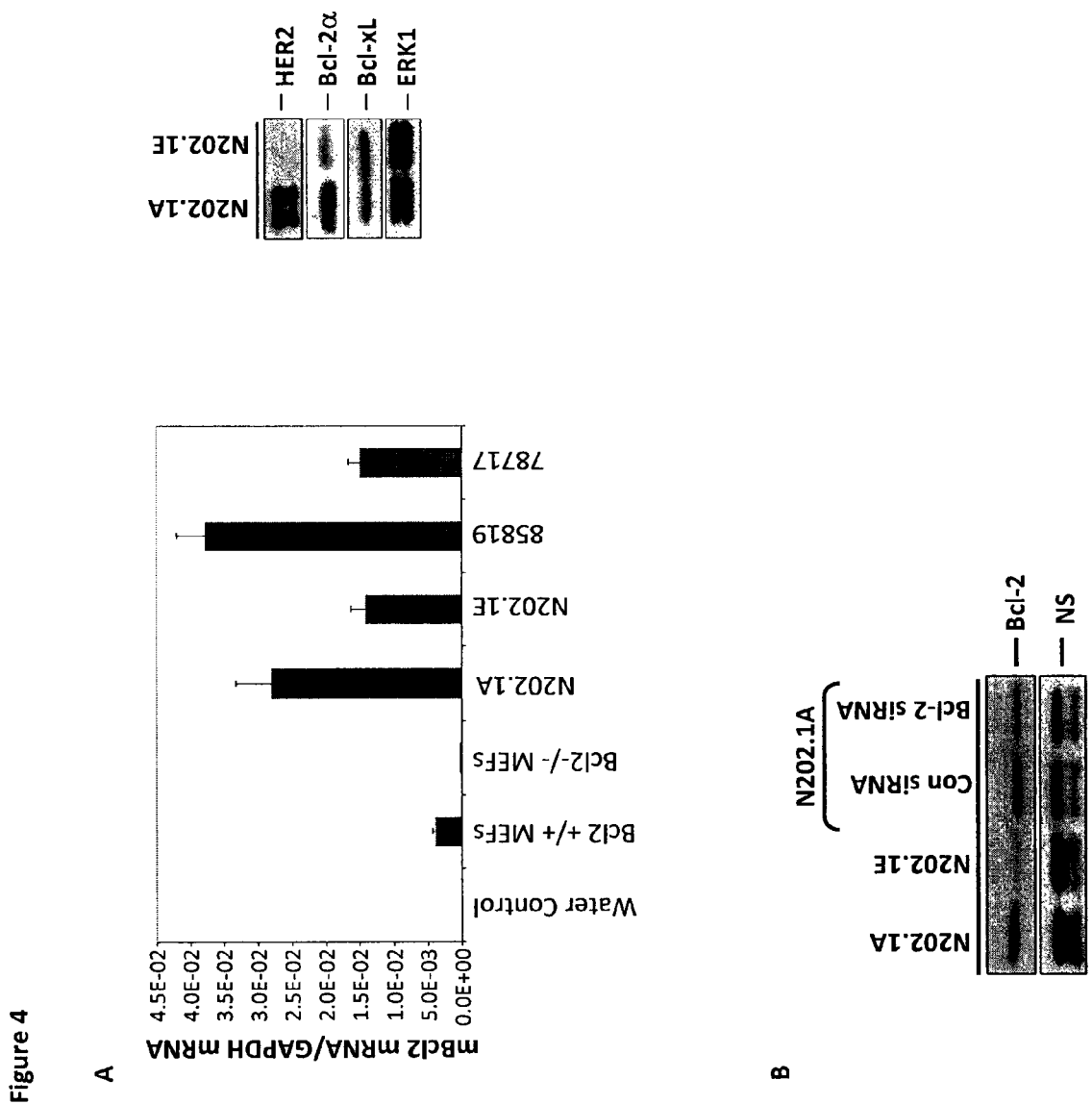
Figure 4:
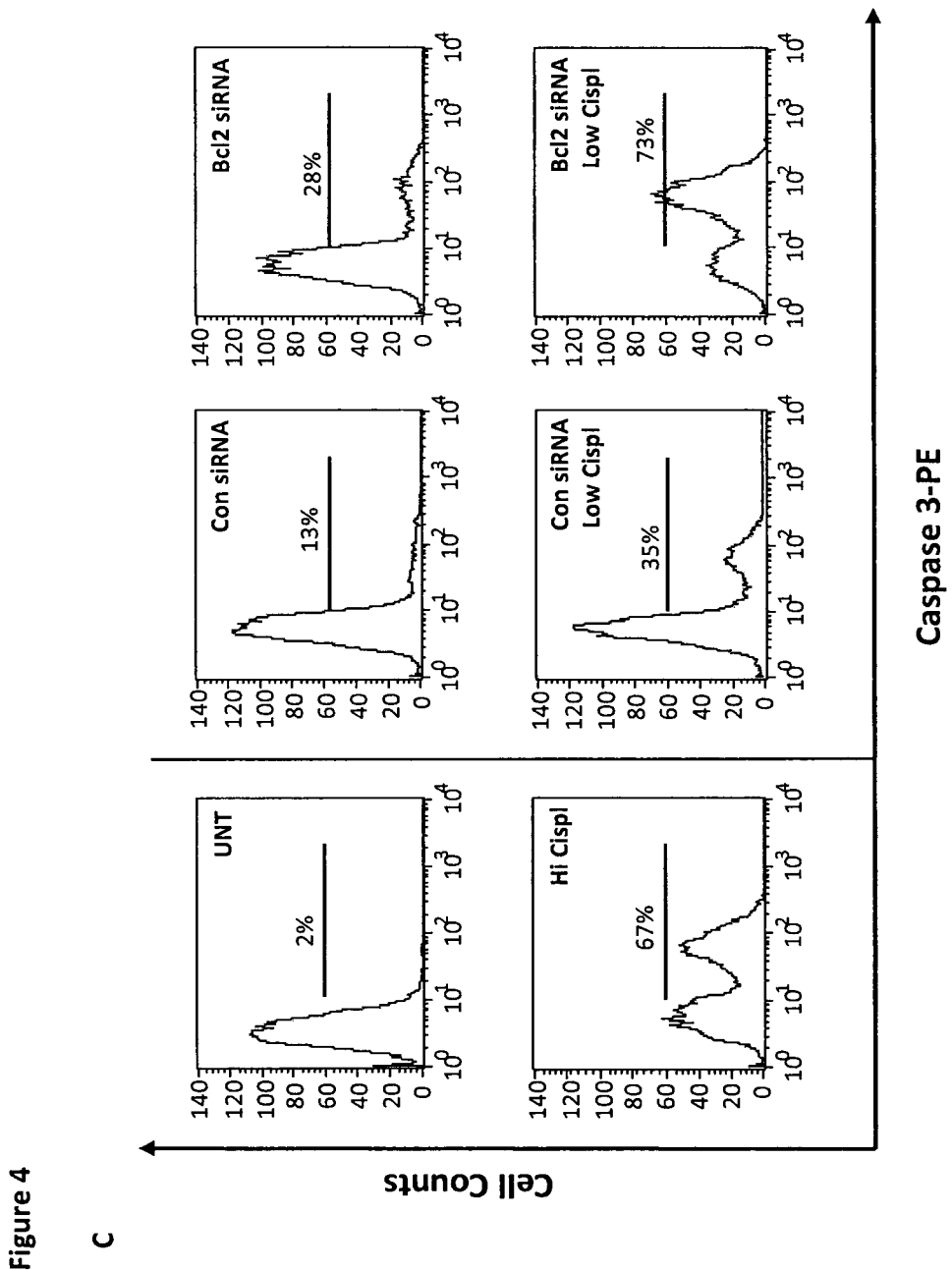

FIGS. 4A-4C: Characterization of Bcl-2 as an siRNA target in HER2-positive cancer cells. (A) Bcl-2 overexpression at the mRNA level (left panel) was measured in HER2-positive (wild-type MEFs, N202.1A, 85819) relative to HER2-negative (Bcl-2−/− MEFs (Kamada S et al., bcl-2 deficiency in mice leads to pleiotropic abnormalities: accelerated lymphoid cell death in thymus and spleen, polycystic kidney, hair hypopigmentation, and distorted small intestine. *Cancer Res.* 55(2):354-9 (1995). PubMed PMID: 7812968), N202.1E, 78717) cells by qRT-PCR. Samples were normalized to GAPDH. Overexpression of Bcl-2 at the protein level (right panel) was measured by western blot of N202.1E and N202.1A cells. The related family member Bcl-xL was not overexpressed at the protein level in HER2-positive cancer cells. ERK was used as a loading control. (B) Knockdown of Bcl-2 after transfection of Bcl-2 siRNA. The Bcl-2 siRNA antisense sequence is 5'-GUAGCCCCUCUGUGA-CAGCUU-3' (SEQ ID NO: 31). (C) Bcl-2 siRNA sensitizes HER2-positive cells to low-dose cisplatin (10 mM), resulting in apoptosis as measured by caspase-3 activation. The percent of apoptotic cells was determined by flow cytometry analysis of caspase-3-PE stained cells. High dose cisplatin (40 mM).

Figure 2:
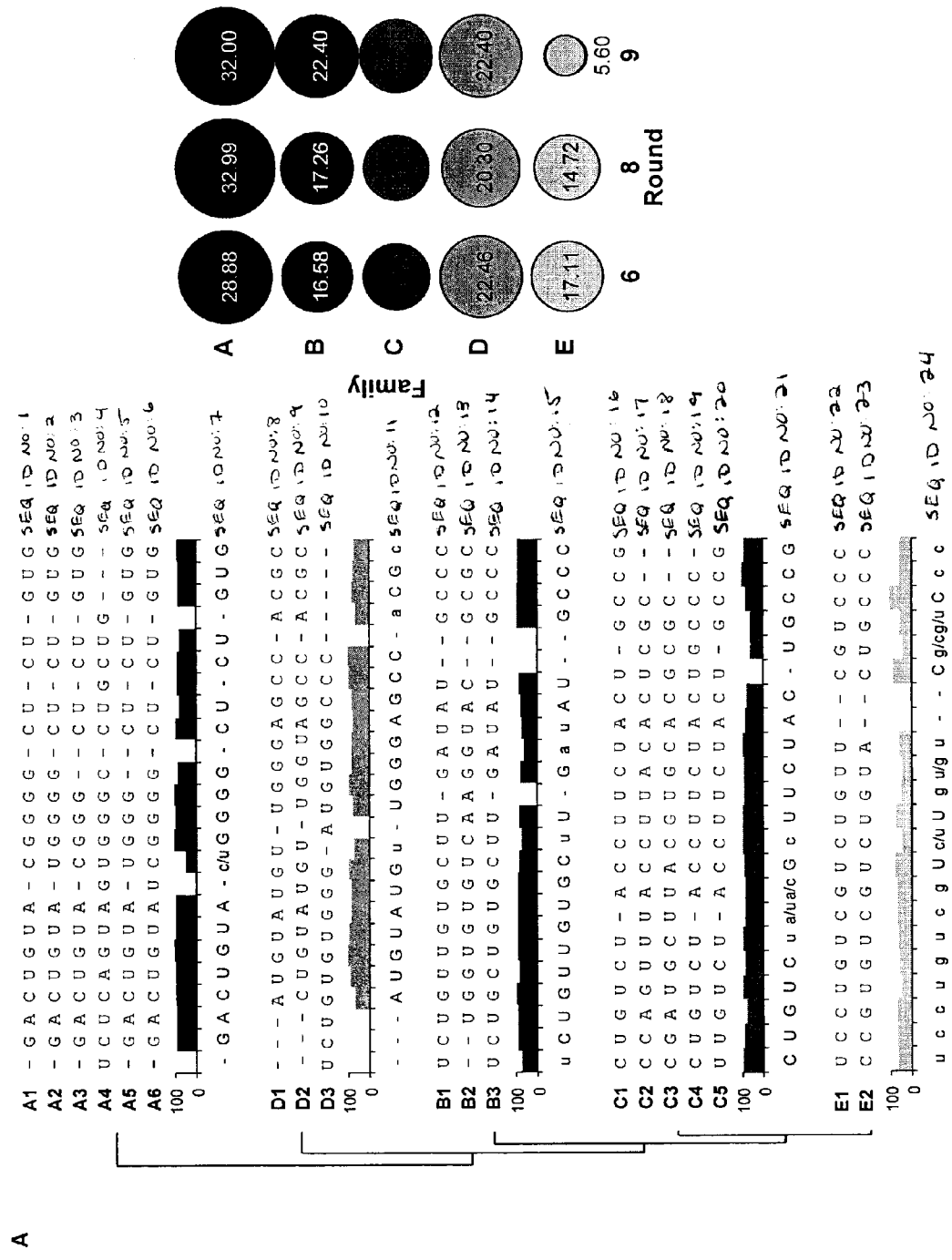
FIGS. 2A-2E: Internalization of single aptamers into HER2-positive cells. (A) Dendrogram of sequence families with representative RNA aptamers and consensus sequence within each family. The consensus sequence of each family was determined and plotted using the distribution of nucleotides at each position (upper case>75%, lower case<75%, lower case/lower case<50%, gap 0%). The distribution (% of total) of sequence families within each round is shown on the right (circles). The sequences are as follows.
Figure 2:
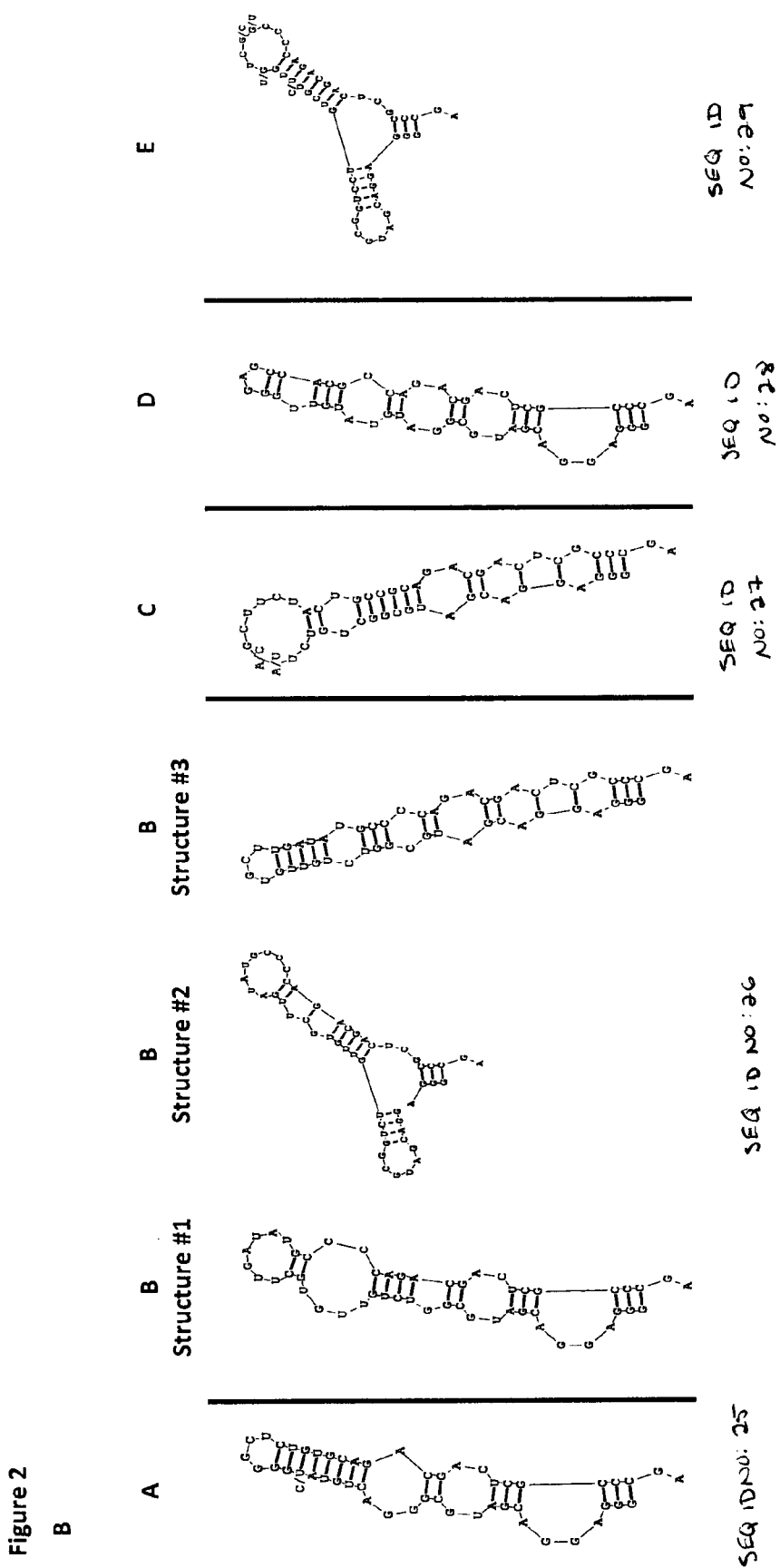
Figure 2:
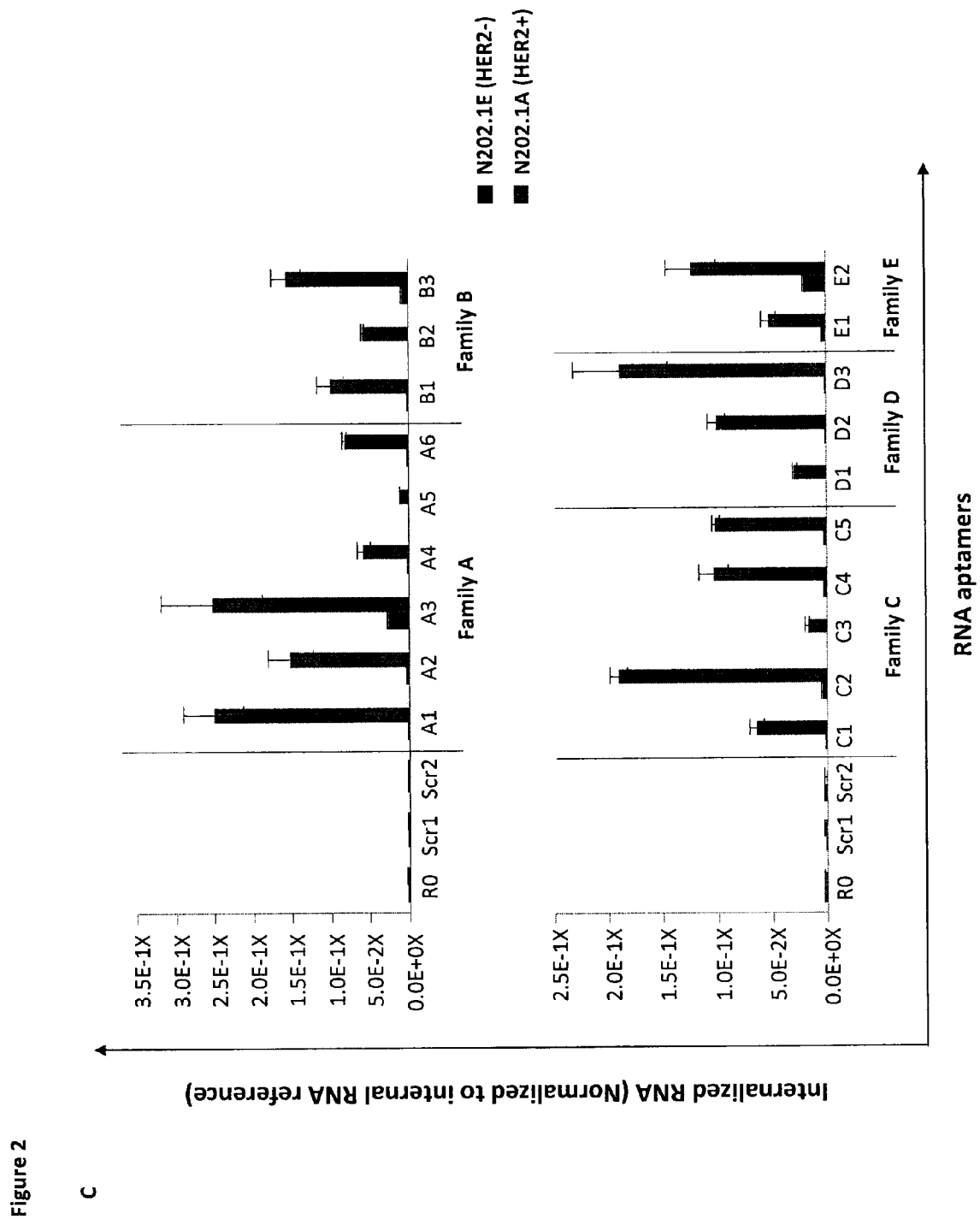
Figure 2:
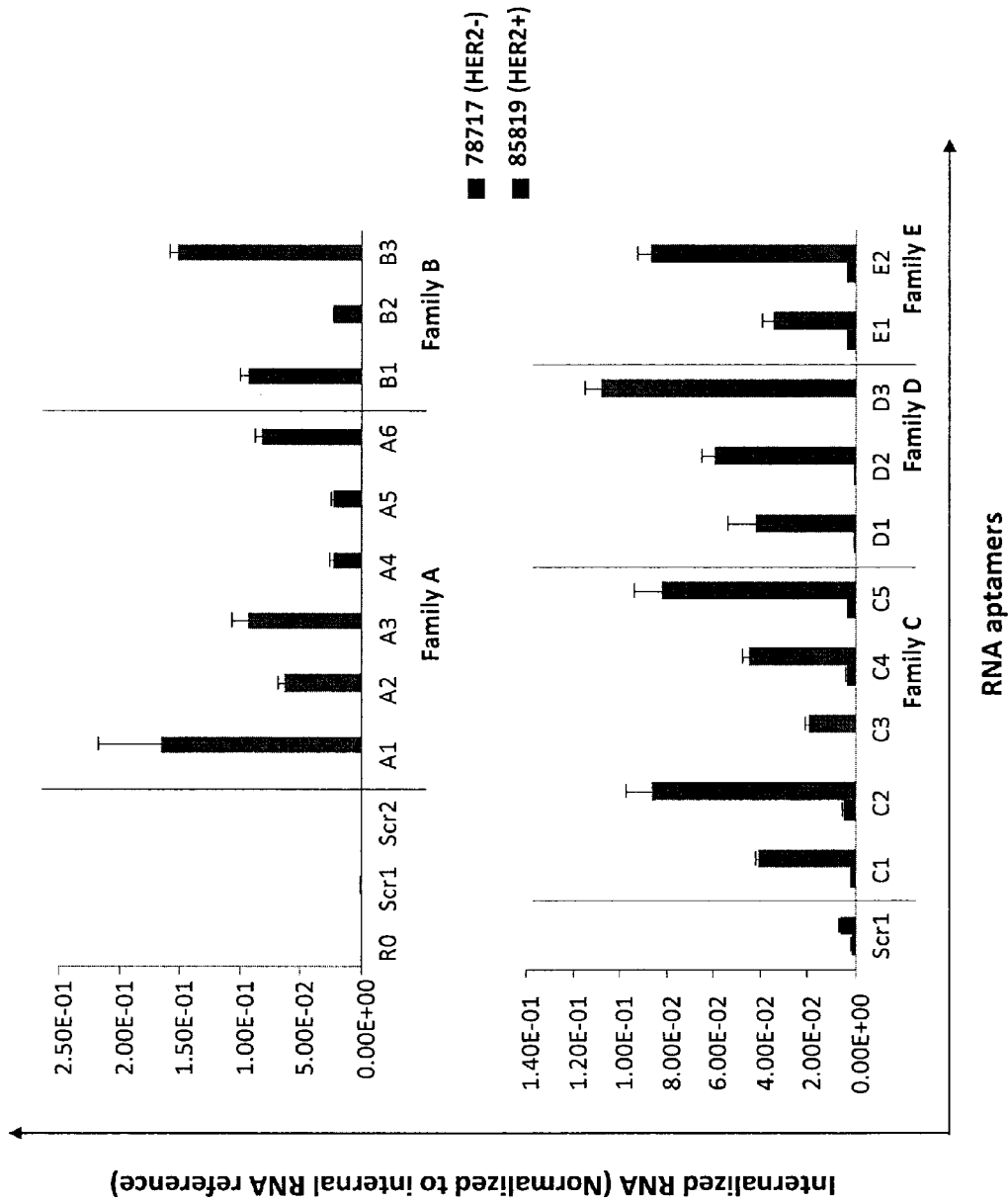
Figure 2:
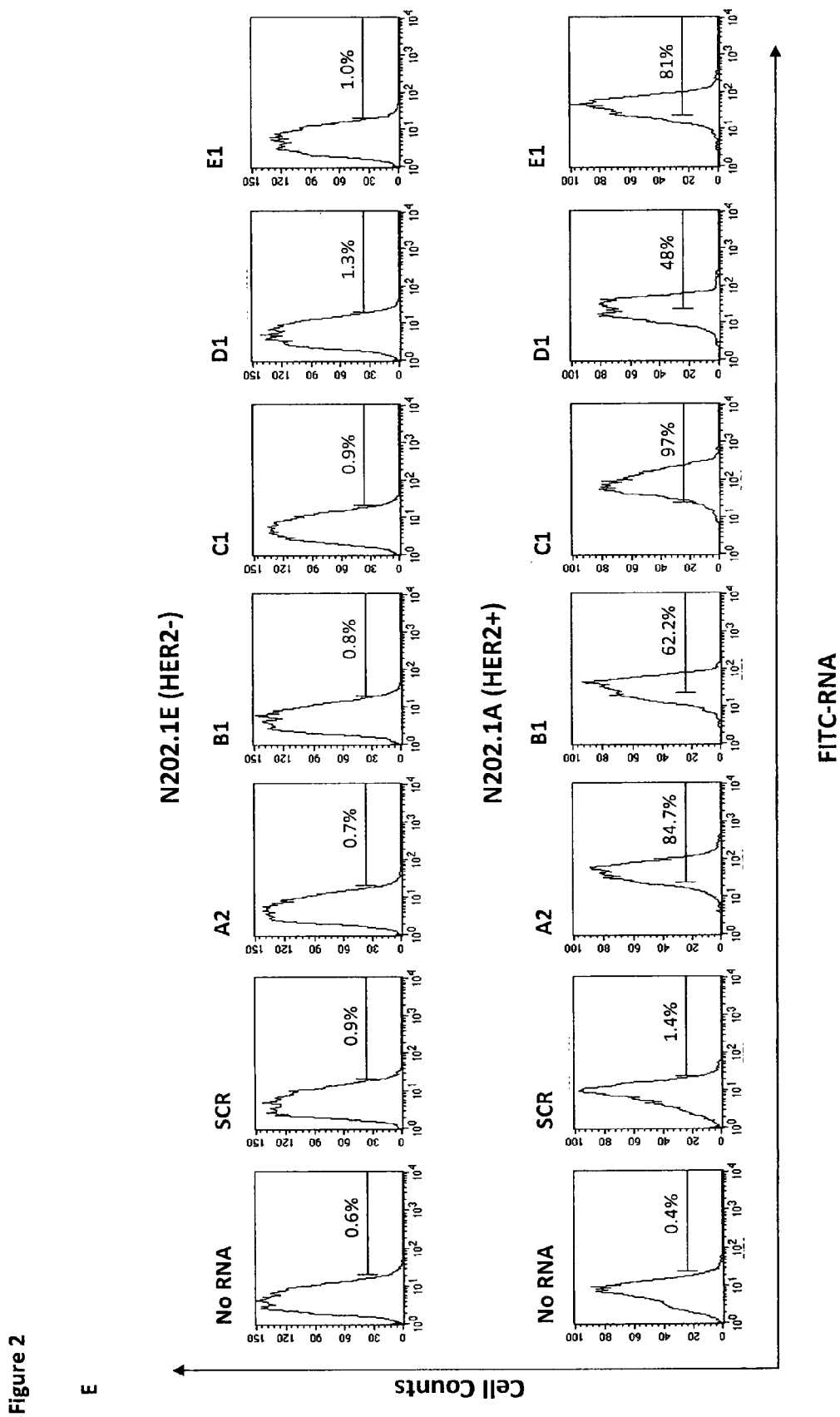

FIGS. 5A-5E: Chimera-mediated death of HER2-positive mammary carcinoma cells. (A) Aptamer:Bcl-2 siRNA chimera secondary structures were predicted using RNAStructure as in FIG. 2. Red nucleotides indicate the Bcl-2 siRNA antisense sequence (5'-GUAGCCCCUCUGUGACAGCUU-3', SEQ ID NO: 31); antisense strand is indicated in black (5'-GCUGUCACAGAGGGGCUACUU-3', SEQ ID NO:30).

| SEQ ID NO | Identifier |
|---|---|
| SEQ ID NO: 32 | A1-Bcl-2 |
| SEQ ID NO: 33 | A2-Bcl-2 |
| SEQ ID NO: 34 | A3-Bcl-2 |
| SEQ ID NO: 35 | B1-Bcl-2 |
| SEQ ID NO: 36 | B2-Bcl-2 |
| SEQ ID NO: 37 | B3-Bcl-2 |
| SEQ ID NO: 38 | C1-Bcl-2 |
| SEQ ID NO: 40 | C3-Bcl-2 |
| SEQ ID NO: 41 | D1-Bcl-2 |
| SEQ ID NO: 42 | D2-Bcl-2 |
| SEQ ID NO: 43 | D3-Bcl-2 |
| SEQ ID NO: 44 | E1-Bcl-2 |

(B) Chimeras were generated by annealing the Bcl-2 antisense sequence to a complementary sequence added to the 3' end of each aptamer. Internalization of aptamer:siRNA chimeras was compared to aptamers alone and analyzed by qRT-PCR as in FIG. 1C. (C) Chimera internalization was tested in normal mouse mammary carcinoma cells (NMuMG) and compared to internalization in N202.1A cells as in (B). (D) Silencing of Bcl-2 at the mRNA level was determined by qRT-PCR after exposure of N202.1A cells to chimeras for 38 and 96 hours. Samples were normalized to GAPDH. (E) N202.1A cells were treated with aptamer:Bcl-2 siRNA chimeras for 72 hours, then with media containing chimeras and low-dose cisplatin (10 µM) for an additional 24 hours. The number of dead cells was determined by trypan blue staining. Cells from (D) were additionally stained with active caspase-3-PE to assess apoptosis. Values are quantitated relative to Bcl-2 siRNA transfection+low-dose cisplatin (100%).

FIGS. 6A and 6B: Validation of methodologies used to isolate internalized aptamers. FIG. 6A. Prostate-specific membrane antigen (PSMA) FAM-A10 aptamer was exposed to PSMA-positive (LNCaP) or PSMA-negative (PC-3) cells at either 4° C. or 37° C., and then cells were washed with either PBS or high salt (0.5M NaCl). Fluorescent intensity was determined by flow cytometry. FIG. 6B. To determine internalization using qRT-PCR, N202.1A cells were incubated with RND 0 library RNA (100 nM) for the indicated times at either 4° C. or 37° C. Cells were washed with either PBS or high salt, and then RNA was recovered and analyzed using qRT-PCR.

Figure 7:
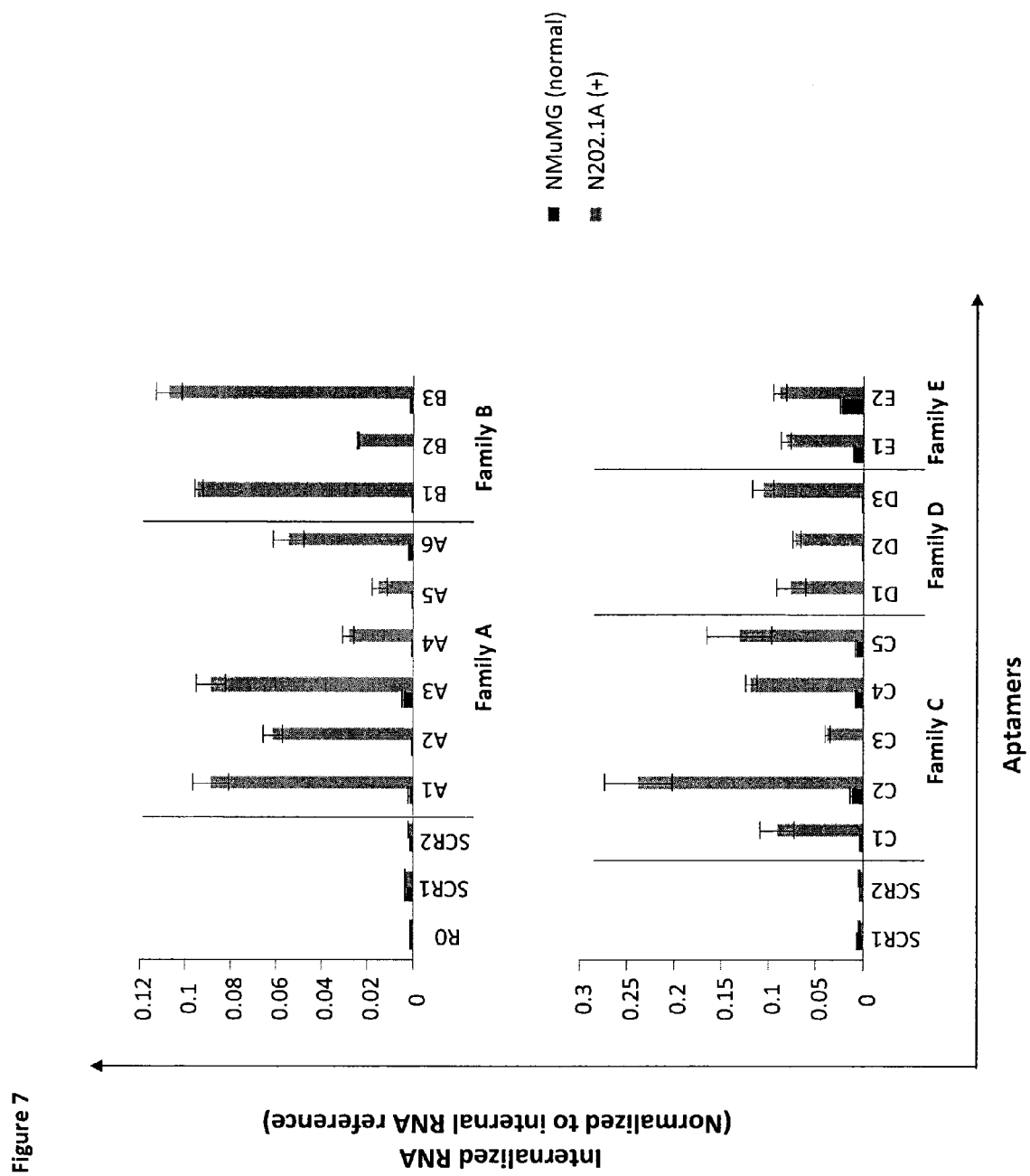

FIG. 7: Specificity of aptamers for HER2+ cancer cells but not normal mammary epithelial cells. Internalization of single aptamers into N202.1A (HER2+ cancer cells) or NMuMG (normal mouse mammary epithelial cells, ATCC) was evaluated by qRT-PCR as in FIG. 2. All samples were normalized to an internal reference (M12-23 aptamer) and to the PCR amplification of each aptamer relative to the SCR control. The inventors assessed the ability of the HER2 aptamers alone to internalize into mouse mammary carcinoma cells expressing HER2 (N202.1A) or normal mouse mammary epithelial cells (NMuMG). These experiments demonstrated that all RNA aptamers selected internalized more efficiently in mammary carcinoma cells expressing HER2 on the cell surface. This finding demonstrates the specificity of targeting of these reagents and suggests that these reagents can be used to target (cytotoxic drugs) predominantly to cancer cells with high HER2 surface expression.

Figure 8:
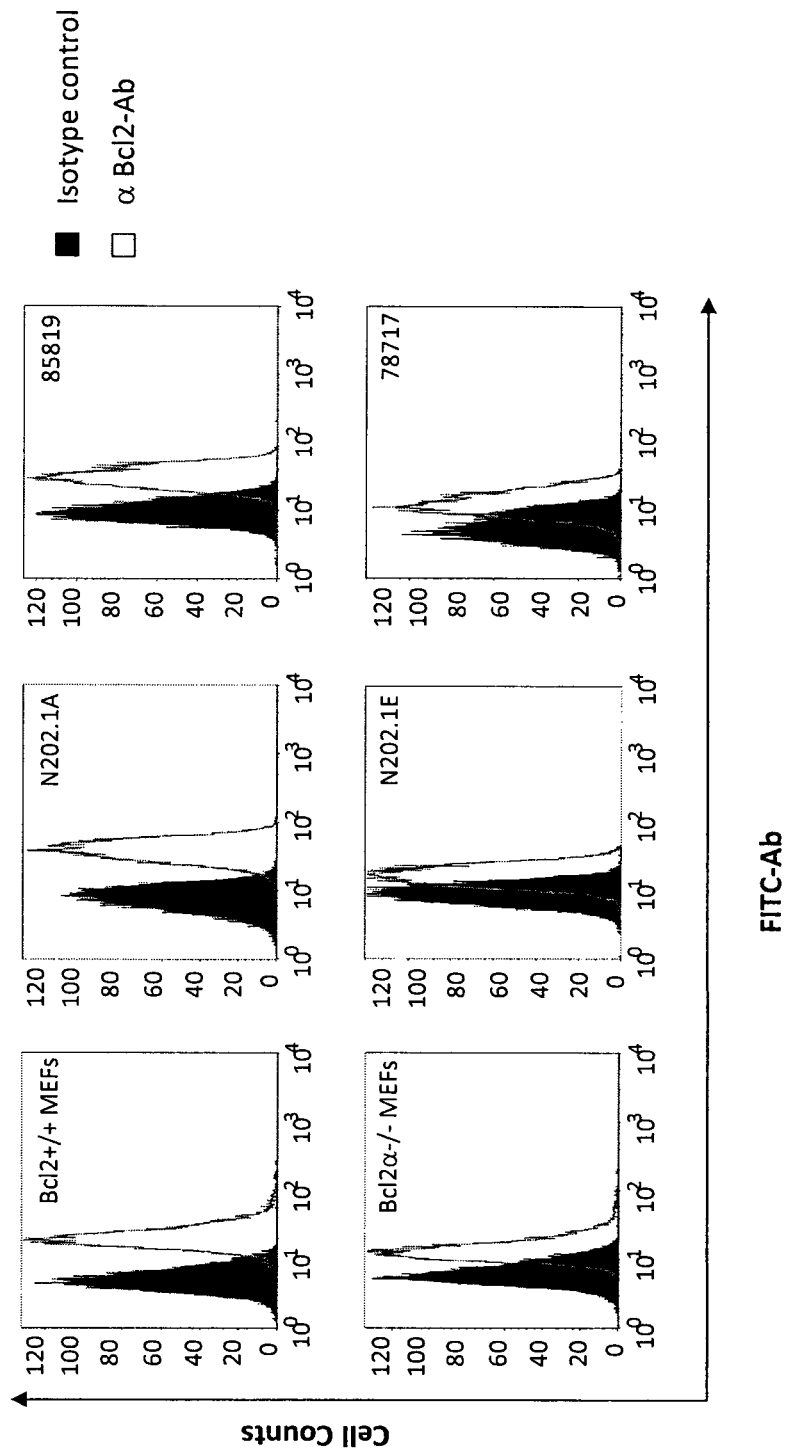

FIG. 8: Expression of Bcl-2 in HER2-positive cancer cells. Cells were permeabilized and stained with FITC-Bcl-2 antibody, and then samples were analyzed by flow cytometry to determine fluorescence intensity.

Figure 9:
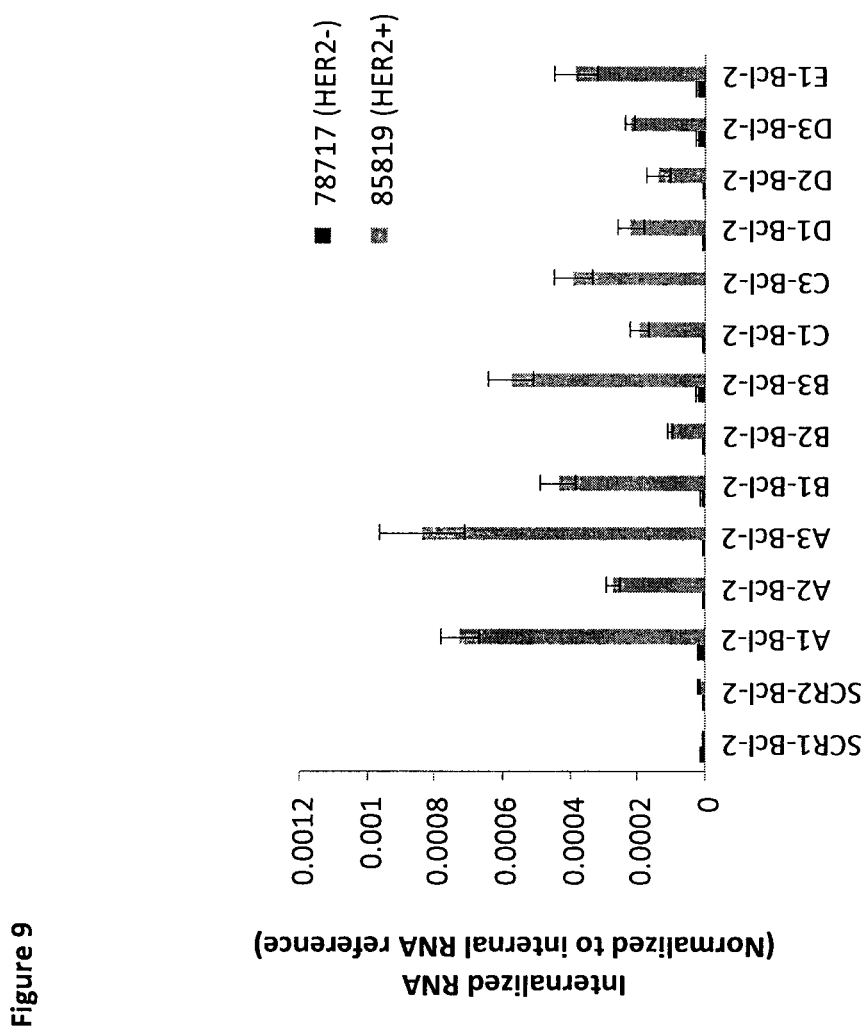

FIG. 9: Internalization of HER2 aptamer:Bcl-2 siRNA chimeras into 78717 and 85819 cells. HER2 aptamers-Bcl2 siRNA chimeras were incubated on either 85919(HER2+) or 78717(HER2−) mouse breast cancer carcinoma cells. Cell internalization was performed as described in FIGS. 5B and 5C. Internalized RNAs were quantitated by qRT-PCR and normalized to an internal RNA reference control. These results demonstrate that the RNAs preferentially internalize into cells expressing HER2 on the cell surface.

DETAILED DESCRIPTION

Modulation of gene expression by endogenous, noncoding RNAs is increasingly appreciated as a mechanism playing a role in eukaryotic development, maintenance of chromatin structure and genomic integrity. Recently, techniques have been developed to trigger RNA interference (RNAi) against specific targets in mammalian cells by introducing exogenously produced or intracellularly expressed siRNAs. These methods have proven to be quick, inexpensive and effective for knockdown experiments in vitro and in vivo. The ability to accomplish selective gene silencing has led to the hypothesis that siRNAs might be employed to suppress gene expression for therapeutic benefit.

Disclosed herein is a strategy that results in substantial silencing of targeted genes via RNAi. Use of this strategy results in markedly diminished in vitro and in vivo expression of targeted genes. This strategy is useful in reducing expression of targeted genes in order to model biological processes or to provide therapy for human diseases. For example, this strategy can be applied to a the treatment of cancer. As used herein the term "substantial silencing" means that the mRNA of the targeted gene is inhibited and/or degraded by the presence of the introduced siRNA, such that expression of the targeted gene is reduced by about 10% to 100% as compared to the level of expression seen when the siRNA is not present. Generally, when a gene is substantially silenced, it will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, 98%, 99% or even 100% reduction expression as compared to when the siRNA is not present. As used herein the term "substantially normal activity" means the level of expression of a gene when an siRNA has not been introduced to a cell.

An embodiment of the invention described herein is an optimized RNA-based therapeutic reagent for the treatment of breast and possibly other solid sarcomas and carcinomas. This reagent consists of two basic components, an RNA aptamer (a structural, synthetic RNA) coupled to a small molecule. The aptamer portion of the reagent serves as a targeting moiety by binding specifically to a cell surface receptor (e.g., HER2) expressed on cancer cells (e.g., breast cancer cells).

Most RNAi-targeted approaches described to date involve complexation of siRNAs with charged peptides (Kumar et al., *Nature* 448(7149):39-43 (2007), Aigner A., *J Biotechnol.* 124(1):12-25 (2006); Meade et al., *Adv Drug Deliv Rev.* 59(2-3):134-40 (2007)), proteins (e.g., antibodies) (Song et al., *Nat. Biotechnol.* 23(6):709-17 (2005); Peer et al., *Proc Natl Acad Sci USA.* 104(10):4095-100 (2007)), or polymers (Rozema et al., *Proc Natl Acad Sci USA.* 104(32):12982-7 (2007); Hu-Lieskovan et al., *Cancer Res.* 65(19):8984-92 (2005); Heidel et al., *Proc Natl Acad Sci USA.* 104(14):5715-21 (2007); Takei et al., *Cancer Res.* 64(10):3365-70 (2004); Takeshita et al., *Cancer Sci.* 97(8):689-96 (2006); Howard et al., *Mol. Ther.* 14(4):476-84 (2006); Pillé et al., *Hum Gene Ther.* 17(10):1019-26 (2006)). While these siRNA-based reagents are proving effective at silencing the targeted genes when administered systemically in experimental animals, their complex formulation complicates large-scale production and regulatory approval. An additional challenge in many cases is that the materials making up the complexes either exhibit toxicity in vivo or have uncertain safety profiles. As a result of these challenges, applications involving the direct local delivery (e.g., eye and lung) of naked or nuclease-resistant (e.g., 2' fluoro modified) siRNA duplexes (Chiu et al., *RNA* 9(9):1034-48 (2003); Layzer et al., *RNA* 10(5):766-71 (2004)) have been the first to be evaluated in clinical trials.

Each year nearly 30% of breast cancer patients will die from metastases or toxic side effects of treatments. Toxic side effects are largely due to inadequate therapeutic targeting specificity. Human epidermal growth factor receptor (HER)-2 is a member of the HER tyrosine kinase family. HER2 expression in breast cancer is associated with an aggressive phenotype and poor prognosis, making it an appealing therapeutic target. Antibody-based HER2 inhibitors are currently the leading treatment for HER2-positive breast cancers. While HER2 antibodies show some growth inhibitory effects, women treated with them develop resistance to the therapy, highlighting the need for novel, more efficient targeted therapies. Importantly, a number of genes responsible for insensitivity or resistance to treatment have been identified. These include other growth factor receptors and established anti-apoptotic genes. Inhibition of these genes with novel therapeutics (e.g., RNA interference) promises to be an effective approach to overcome resistance in HER2-positive cancers. However, global inhibition of many of these genes is likely to result in serious unwanted side effects. Approaches for selectively silencing these genes in HER2-positive cancer cells are therefore highly desirable.

Aptamer Portion

Aptamers are single stranded oligonucleotides that can naturally fold into different 3-dimensional structures, which have the capability of binding specifically to biosurfaces, a target compound or a moiety. The term "conformational change" refers to the process by which a nucleic acid, such as an aptamer, adopts a different secondary or tertiary structure. The term "fold" may be substituted for conformational change.

Aptamers have advantages over more traditional affinity molecules such as antibodies in that they are very stable, can be easily synthesized, and can be chemically manipulated with relative ease. Aptamer synthesis is potentially far cheaper and reproducible than antibody-based diagnostic tests. Aptamers are produced by solid phase chemical synthesis, an accurate and reproducible process with consistency among production batches. An aptamer can be produced in large quantities by polymerase chain reaction (PCR) and once the sequence is known, can be assembled from individual naturally occurring nucleotides and/or synthetic nucleotides. Aptamers are stable to long-term storage at room temperature, and, if denatured, aptamers can easily be renatured, a feature not shared by antibodies. Furthermore, aptamers have the potential to measure concentrations of ligand in orders of magnitude lower (parts per trillion or even quadrillion) than those antibody-based diagnostic tests. These characteristics of aptamers make them attractive for diagnostic applications.

Aptamers are typically oligonucleotides that may be single stranded oligodeoxynucleotides, oligoribonucleotides, or modified oligodeoxynucleotide or oligoribonucleotides. The term "modified" encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-; 2-O-alkyl; 2-O-allyl; 2'-S-alkyl; 2'-S-allyl; 2'-fluoro-; 2'-halo or 2-azido-ribose, carbocyclic sugar analogues a-anomeric sugars; epimeric sugars such as arabinose, xyloses or lyxoses, pyranose sugars, furanose sugars, and sedoheptulose.

Modified nucleotides are known in the art and include, by example and not by way of limitation, alkylated purines and/or pyrimidines; acylated purines and/or pyrimidines; or other heterocycles. These classes of pyrimidines and purines are known in the art and include, pseudoisocytosine; N4, N4-ethanocytosine; 8-hydroxy-N6-methyladenine; 4-acetylcytosine, 5-(carboxyhydroxylmethyl)uracil; 5-fluorouracil; 5-bromouracil; 5-carboxymethylaminomethyl-2-thiouracil; 5-carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2-methylthio-N6-isopentenyladenine; uracil-5-oxyacetic acid methyl ester; psueouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpsuedouracil; 1-methylguanine; 1-methylcytosine.

The aptamers of the invention are synthesized using conventional phosphodiester linked nucleotides and synthesized using standard solid or solution phase synthesis techniques which are known in the art. Linkages between nucleotides may use alternative linking molecules. For example, linking groups of the formula P(O)S, (thioate); P(S)S, (dithioate); P(O)NR'2; P(O)R'; P(O)OR6; CO; or CONR'2 wherein R is H (or a salt) or alkyl (1-12C) and R6 is alkyl (1-9C) is joined to adjacent nucleotides through —O— or —S—.

In certain embodiments of the present invention, the aptamer portion binds to Human Epidermal growth factor Receptor 2 (HER2). In certain embodiments, modifications are made to the aptamer portion. Additional modifications to the aptamer portion include 2'O-methyl modification of the pyrimidines. In other embodiments, all of the nucleotides in the aptamer are 2'O-methyl modified. Alternatively, the pyrimidines, or all the nucleotides, may be modified with 2' fluoros (both pyrimidines and purines). Additional modifications to the nucleotides in the aptamer include large molecular weight conjugates like pegylation, lipid-based modifications (e.g., cholesterol) or nanoparticles (e.g., PEI or chitosan) to improve the pharmacokinetic/dynamic profile of the chimera.

In certain embodiments, modifications are introduced into the stem sequence in the aptamer. Different nucleotides can be used as long as the structure of the stem is retained.

Accordingly, in certain embodiments, the present invention provides an aptamer molecule not more than 55 nucleotides in length comprising the nucleic acid sequence 5'-GG-GAGGACGAUGCGG-R$^1$-CAGACGACUCGCCCGA-3' (SEQ ID NO: 45), wherein R$^1$ is (n)$_x$ where each n represents any nucleotide, and wherein x is an integer from 19 to 21. In certain embodiments, R$^1$ is

```
                                   (A1, SEQ ID NO: 1)
          GACUGUACGGGGCUCUGUG, (A2, SEQ ID NO: 2)
          GACUGUAUGGGGCUCUGUG, (A3, SEQ ID NO: 3)
          GACUGUACGGGCUCUGUG, (A4, SEQ ID NO: 4)
          UCUCAGUAGUGGGCCUGCUG, (A5, SEQ ID NO: 5)
          GACUGUAUGGGCUCUGUG, (A6, SEQ ID NO: 6)
          GACUGUAUCGGGGCUCUGUG, (A-consensus, SEQ ID NO: 7)
          GACUGUAYGGGCUCUGUG, (D1, SEQ ID NO: 8)
          AUGUAUGUUGGGAGCCACGC,
```

```
                    (D2, SEQ ID NO: 9)
CUGUAUGUUGGUAGCCACGC, (D3, SEQ ID NO: 10)
UCUGUGUGGGAUGUGGCCC, (D-consensus, SEQ ID NO: 11)
AUGUAUGUUGGGAGCCACGC, (B1, SEQ ID NO: 12)
UCUGUUGUGCUUGAUAUGCCC, (B2, SEQ ID NO: 13)
UGGUGUGUCAAGGUACGCGC, (B3, SEQ ID NO: 14)
UCUGCUGUGCUUGAUAUGCCC, (B-consensus, SEQ ID NO: 15)
UCUGUUGUGCUUGAUAUGCCC, (C1, SEQ ID NO: 16)
CUGUCUACCUUCUACUGCCG, (C2, SEQ ID NO: 17)
CCAGUUUACCUUACACUCGC, (C3, SEQ ID NO: 18)
CGAUGCUUACGUGCACGCGC, (C4, SEQ ID NO: 19)
CUGUCUACCUUCUACUGCCC, (C5, SEQ ID NO: 20)
UUGUCUACCUUCUACUGCCG, (C-consensus, SEQ ID NO: 21)
CUGUCUWMGCUUCUACUGCCG, (E1, SEQ ID NO: 22)
UCCUGUCGUCUGUUCGUCCC, (E2, SEQ ID NO: 23)
CCGUGUCGUCUGUACUGCCC,
or (E-consensus, SEQ ID NO: 24)
UCCUGUCGUYUGKUCSKCCC.
```

In certain embodiments, the aptamer comprises nucleic acid 5'-GGGAGGACGAUGCGGGACUGUAYGGGGCUCUGUGCAGACGACUCGCCCGA-3' (aptamer A, SEQ ID NO: 25); 5'-GGGAGGACGAUGCGGUCUGUUGUGCUUGAUAUGCCCCAGACGACUCGCCCGA-3' (aptamer B, SEQ ID NO: 26); 5'-GGGAGGACGAUGCGGCUGUCUWMGCUUCUACUGCCGCAGACGACUCGCCCGA-3' (aptamer C, SEQ ID NO: 27); 5'-GGGAGGACGAUGCGGAUGUAUGUUGGGAGCCACGCCAGACGACUCGCCCGA-3' (aptamer D, SEQ ID NO: 28); or 5'-GGGAGGACGAUGCGGUCCUGUCGUYUGKUCSKCCCCAGACGACUCGCC CGA-3' (aptamer E, SEQ ID NO: 29).

Small Molecule Portion

The aptamers of the present invention can be operably linked to one or more small molecule entities. In certain embodiments, the entity is a fluorescent tag, affinity tag, a protein, a solid substrate, a cell surface, or a cellular component. In certain embodiments, the cellular component is a cell wall or cell membrane. In certain embodiments, the solid substrate is a component of silica, cellulose, cellulose acetate, nitrocellulose, nylon, polyester, polyethersulfone, polyolefin, or polyvinylidene fluoride, or combinations thereof. In certain embodiments, the solid substrate is a filter, magnetic bead, metal oxide, latex particle, microtiter plates, polystyrene bead, or CD-ROM.

In certain embodiments, the aptamer is linked to the entity by means of a linker. In certain embodiments, the linker is a binding pair. In certain embodiments, the "binding pair" refers to two molecules which interact with each other through any of a variety of molecular forces including, for example, ionic, covalent, hydrophobic, van der Waals, and hydrogen bonding, so that the pair have the property of binding specifically to each other. Specific binding means that the binding pair members exhibit binding to each other under conditions where they do not bind to another molecule. Examples of binding pairs are biotin-avidin, hormone-receptor, receptor-ligand, enzyme-substrate, IgG-protein A, antigen-antibody, and the like. In certain embodiments, a first member of the binding pair comprises avidin or streptavidin and a second member of the binding pair comprises biotin. In certain embodiments, the aptamer is linked to the entity by means of a covalent bond.

The entity, for example, may additionally or alternatively, be a detection means. A number of "molecular beacons" (such as fluorescence compounds) can be attached to aptamers to provide a means for signaling the presence of and quantifying a target chemical or biological agent. Other exemplary detection labels that could be attached to the aptamers include biotin, any fluorescent dye, amine modification, horseradish peroxidase, alkaline phosphatase, etc.

In certain embodiments, the aptamer is operably linked to a detection means and to a solid substrate. For example, the aptamer may be linked to a fluorescent dye and to a magnetic bead.

The small molecule portion of the ligand can be RNAi molecules, such as siRNA sequences, miRNAs, small molecule inhibitors, chelators for housing radionuclides (for diagnostic/imaging applications as well as development of targeted radiotherapies), nanoparticles containing all of the above plus DNA vectors and/or mRNA sequences, depending on the use of the ligand as a diagnostic agent or as a therapeutic agent. In certain embodiments, the small molecule is an RNAi molecule, such as an siRNA or an miRNA. The RNAi portion, upon delivery to the targeted cells, induces the depletion of cancer cell survival factors, leading to the death of the cancer cells. In certain embodiments, the siRNA portion binds to Bcl-2 within the cell, inhibiting the gene's activity. After the aptamer binds HER2 expressed on the surface of the cell, the complex is taken into the cell by endocytosis. The molecule is then cleaved by Dicer, an endonuclease, and is incorporated into the RNA-Induced Silencing Complex (RISC) where it mediates Bcl-2 degradation. In certain embodiments, the present invention provides a Bcl-2 RNAi molecule, or the complement thereof. As used herein a Bcl-2 RNAi molecule is an RNA molecule of between 22 and 30 nucleotides substantially silences Bcl-2. In certain embodiments, the Bcl-2 RNAi comprises nucleic acid 5'-GCUGUCACAGAGGGGCUACUU-3' (SEQ ID NO:30). In certain embodiments, the present invention provides a nucleic acid duplex comprising nucleic acid 5'-GCUGUCACAGAGGGGCUACUU-3' (SEQ ID NO:30) hybridized to nucleic acid 5'-GUAGCCCCUCUGUGACAGCUU-3' (SEQ ID NO:31).

Linking Molecules

Chemistries that can be used to link molecules to the aptamer are known in the art, such as disulfide linkages, amino linkages, covalent linkages, etc. Additional linkages and modifications can be found on the world-wide-web at trilinkbiotech.com/products/oligo/oligo_modifications.asp.

Conjugates

In certain embodiments, the present invention provides a conjugate comprising 5'-GCUGUCACAGAGGGGCUACUU-3' (SEQ ID NO:30) operably linked to an aptamer molecule not more than 55 nucleotides in length comprising the nucleic acid sequence 5'-GGGAGGACGAUGCGG-R[1]-CAGACGACUCGCCCGA-3' (SEQ ID NO: 45), wherein R' is (n)$_x$ where each n represents any nucleotide, and wherein x is an integer from 19 to 21. In certain embodiments, the conjugate consisting of 5'-GGGAGGACGAAUGCGG-GACUGUACGGGGCUCUGUGCAGACGACUCGCC CGAGCUGUCACAGAGGGGCUACUU-3' (A1-Bcl-2, SEQ ID NO:32); 5'-GGGAGGACGAUGCGGGACU-GUAUGGGGCUCUGUGCAGACGACUCGCCC GAGCUGUCACAGAGGGGCUACUU-3' (A2-Bcl-2, SEQ ID NO:33); 5'-GGGAGGACGAUGCGGGACU-GUACGGGCUCUGUGCAGACGACUCGCCCG AGCU-GUCACAGAGGGGCUACUU-3' (A3-Bcl-2, SEQ ID NO:34); 5'-GGGAGGACGAUGCGGUCUGUUGUGCU-UGAUAUGCCCCAGACGACUCGC CCGAGCUGUCA-CAGAGGGGCUACUU-3' (B1-Bcl-2, SEQ ID NO:35); 5'-GGGAGGACGAUGCGGUGGUGUGUCAAG-GUACGCGCCAGACGACUCGCC CGAGCUGUCACA-GAGGGGCUACUU-3' (B2-Bcl-2, SEQ ID NO:36); 5'-GG-GAGGACGAUGCGGUCUGCUGUGCUUGAUAUGCC CCAGACGACUCGC CCGAGCUGUCACAGAGGGGC-UACUU-3' (B3-Bcl-2, SEQ ID NO:37); 5'-GGGAGGAC-GAUGCGGCUGUCUACCUUCUACUGCCG-CAGACGACUCGCC CGAGCUGUCACAGAGGGGCUACUU-3' (C1-Bcl-2, SEQ ID NO:38); 5'-GGGAGGACGAUGCGGCGAUGCU-UACGUGCACGCGCCAGACGAACUCGC CCGAGCU-GUCACAGAGGGGCUACUU-3' (C2-Bcl-2, SEQ ID NO:39); 5'-GGGAGGACGAUGCGGCGAUGCU-UACGUGCACGCGCCAGACGACUCGCC CGAGCU-GUCACAGAGGGGCUACUU-3' (C3-Bcl-2, SEQ ID NO:40); 5'-GGGAGGACGAUGCGGAUGUAUGUUGG-GAGCCACGCCAGACGACUCGCC CGAGCUGUCACA-GAGGGGCUACUU-3' (D1-Bcl-2, SEQ ID NO:41); 5'-GG-GAGGACGAUGCGGCUGUAUGUUGGUAGCCACGC CAGACGACUCGCC CGAGCUGUCACAGAGGGGC-UACUU-3' (D2-Bcl-2, SEQ ID NO:42); 5'-GGGAGGAC-GAUGCGGUCUGUGUGGGAUGUGGCCCCA-GACGACUCGCCC GAGCUGUCACAGAGGGGCUACUU-3' (D3-Bcl-2, SEQ ID NO:43); or 5'-GGGAGGACGAUGCGGUCCUGUCGU-CUGUUCGUCCCAGACGACUCGCCC GAGCUGUCA-CAGAGGGGCUACUU-3' (E1-Bcl-2, SEQ ID NO:44). In certain embodiments, the conjugate is hybridized to 5'-GUAGCCCUCUGUGACAGCUU-3' (SEQ ID NO:31).

Detection and Amplification Methods

The present invention provides methods for detecting HER2 in a sample or in vivo. For example, one can contact a sample with an aptamer as described herein or the composition as described herein to form bound HER2, and detecting the presence or the quantity of bound HER2. Alternatively, aptamers or compositions can be administered in vivo to a patient (e.g. injected in situ into a tumor). In certain embodiments, the bound HER2 is detected by means of PCR, nuclear magnetic resonance, fluorescent capillary electrophoresis, lateral flow devices, colorimetry, chemiluminescence, fluorescence, southsester blots, microarrays, or ELISA.

In one embodiment of the present invention, the method also involves contacting the sample with at least one aptamer to form a hybridized nucleic acid and detecting the hybridized nucleic acid. In one embodiment, the detection is by amplification. "Amplifying" utilizes methods such as the polymerase chain reaction (PCR), ligation amplification (or ligase chain reaction, LCR), strand displacement amplification, nucleic acid sequence-based amplification, and amplification methods based on the use of Q-beta replicase. These methods are well known and widely practiced in the art. Reagents and hardware for conducting PCR are commercially available. In one embodiment of the present invention, at least one type of aptamer is immobilized on a solid surface.

The methods of the present invention can be used to detect the presence of HER2 in a sample.

According to the methods of the present invention, the amplification of HER2 present in a sample may be carried out by any means known to the art. Examples of suitable amplification techniques include, but are not limited to, polymerase chain reaction (including, for RNA amplification, reverse-transcriptase polymerase chain reaction), ligase chain reaction, strand displacement amplification, transcription-based amplification, self-sustained sequence replication (or "3SR"), the Qβ replicase system, nucleic acid sequence-based amplification (or "NASBA"), the repair chain reaction (or "RCR"), and boomerang DNA amplification (or "BDA").

The bases incorporated into the amplification product may be natural or modified bases (modified before or after amplification), and the bases may be selected to optimize subsequent electrochemical detection steps.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized that is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques. Where the nucleic acid to be amplified is RNA, amplification may be carried out by initial conversion to DNA by reverse transcriptase in accordance with known techniques.

Strand displacement amplification (SDA) may be carried out in accordance with known techniques. For example, SDA may be carried out with a single amplification primer or a pair of amplification primers, with exponential amplification being achieved with the latter. In general, SDA amplification primers comprise, in the 5' to 3' direction, a flanking sequence (the DNA sequence of which is noncritical), a restriction site for the restriction enzyme employed in the reaction, and an oligonucleotide sequence (e.g., an oligonucleotide probe of the present invention) that hybridizes to the target sequence to be amplified and/or detected. The flanking sequence, which serves to facilitate binding of the restriction enzyme to the recognition site and provides a DNA polymerase priming site after the restriction site has been nicked, is about 15 to 20 nucleotides in length in one embodiment. The restriction site is functional in the SDA reaction. The oligonucleotide probe portion is about 13 to 15 nucleotides in length in one embodiment of the invention.

Ligase chain reaction (LCR) is also carried out in accordance with known techniques. In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

Diagnostic techniques that are useful in the methods of the invention include, but are not limited to direct DNA sequencing, pulsed-field gel electrophoresis (PFGE) analysis, allele-specific oligonucleotide (ASO), dot blot analysis and denaturing gradient gel electrophoresis, and are well known to the artisan.

The sample may be contacted with the aptamer in any suitable manner known to those skilled in the art. For example, the sample may be solubilized in solution, and contacted with the aptamer by solubilizing the aptamer in solution with the sample under conditions that permit binding. Suitable conditions are well known to those skilled in the art. Alternatively, the sample may be solubilized in solution with the aptamer immobilized on a solid support, whereby the sample may be contacted with the aptamer by immersing the solid support having the aptamer immobilized thereon in the solution containing the sample.

General Terminology

"Synthetic" aptamers are those prepared by chemical synthesis. The aptamers may also be produced by recombinant nucleic acid methods.

As used herein, the term "nucleic acid" and "polynucleotide" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

By "fragment" or "portion" is meant a full length or less than full length of the nucleotide sequence.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have in at least one embodiment 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

The term "gene" is used broadly to refer to any segment of nucleic acid associated with a biological function. Genes include coding sequences and/or the regulatory sequences required for their expression. For example, gene refers to a nucleic acid fragment that expresses mRNA, functional RNA, or a specific protein, including its regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters. In addition, a "gene" or a "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

"Naturally occurring," "native" or "wild type" is used to describe an object that can be found in nature as distinct from being artificially produced. For example, a nucleotide sequence present in an organism (including a virus), which can be isolated from a source in nature and which has not been intentionally modified in the laboratory, is naturally occurring. Furthermore, "wild-type" refers to the normal gene, or organism found in nature without any known mutation.

"Homology" refers to the percent identity between two polynucleotides or two polypeptide sequences. Two DNA or polypeptide sequences are "homologous" to each other when the sequences exhibit at least about 75% to 85% (including 75%, 76%, 77%, 78%, 79%, 80%, 81%, 82%, 83%, 84%, and 85%), at least about 90%, or at least about 95% to 99% (including 95%, 96%, 97%, 98%, 99%) contiguous sequence identity over a defined length of the sequences.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information (see the World Wide Web at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When using BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the World Wide Web at ncbi.nlm.nih.gov. Alignment may also be performed manually by visual inspection.

For purposes of the present invention, comparison of nucleotide sequences for determination of percent sequence identity to the sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by a BLAST program.

(c) As used herein, "sequence identity" or "identity" in the context of two nucleic acid sequences makes reference to a specified percentage of residues in the two sequences that are the same when aligned for maximum correspondence over a specified comparison window, as measured by sequence comparison algorithms or by visual inspection. When percentage of sequence identity is used in reference to proteins, it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%; at least 80%, 81%, 82%, 83%, 84%, 85%, 86%, 87%, 88%, or 89%; at least 90%, 91%, 92%, 93%, or 94%; or even at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code.

(e)(ii) For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched nucleic acid. Specificity is typically the function of post-hybridization washes, the critical factors being the ionic strength and temperature of the final wash solution. For DNA-DNA hybrids, the $T_m$ can be approximated from the equation of Meinkoth and Wahl: $T_m$ 81.5° C.+16.6 (log M)+0.41 (% GC)−0.61 (% form)−500/L. M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

"Operably-linked" nucleic acids refers to the association of nucleic acid sequences on single nucleic acid fragment so that the function of one is affected by the other, e.g., an arrangement of elements wherein the components so described are configured so as to perform their usual function. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

The terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. For example, "isolated nucleic acid" may be a DNA molecule containing less than 31 sequential nucleotides that is transcribed into an RNAi molecule. Such an isolated RNAi molecule may, for example, form a hairpin structure with a duplex 21 base pairs in length that is complementary or hybridizes to a sequence in a gene of interest, and remains stably bound under stringent conditions (as defined by methods well known in the art, e.g., in Sambrook and Russell, 2001). Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

In addition to a DNA sequence encoding a siRNA, the nucleic acid molecules of the invention include double-stranded interfering RNA molecules, which are also useful to inhibit expression of a target gene.

As used herein, the term "recombinant nucleic acid," e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome that has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. Therefore, "recombinant DNA" includes completely synthetic DNA sequences, semi-synthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

The terms "protein," "peptide" and "polypeptide" are used interchangeably herein. As used herein, the terms "a" or "an" are used to mean "one or more."

To accomplish intracellular expression of the therapeutic RNAi molecules, an RNA molecule is constructed containing two complementary strands or a hairpin sequence (such as a 21-bp hairpin) representing sequences directed against the gene of interest. The RNAi molecule, or a nucleic acid encoding the RNAi molecule, is introduced to the target cell, such as a diseased brain cell. The RNAi molecule reduces target mRNA and protein expression.

The construct encoding the therapeutic RNAi molecule is configured such that the one or more strands of the RNAi molecules are encoded by a nucleic acid that is immediately contiguous to a promoter. In one example, the promoter is a pol II promoter. If a pol II promoter is used in a particular construct, it is selected from readily available pol II promoters known in the art, depending on whether regulatable, inducible, tissue or cell-specific expression of the siRNA is desired. The construct is introduced into the target cell, allowing for diminished target-gene expression in the cell.

The present invention provides an expression cassette containing an isolated nucleic acid sequence encoding an RNAi molecule targeted against a gene of interest. The RNAi molecule may form a hairpin structure that contains a duplex structure and a loop structure. The loop structure may be the aptamer portion. The duplex is less than 30 nucleotides in length, such as from 19 to 25 nucleotides. The RNAi molecule may further contain an overhang region. Such an overhang may be a 3' overhang region or a 5' overhang region. The overhang region may be, for example, from 1 to 6 nucleotides in length. The expression cassette may further contain a pol II promoter, as described herein. Examples of pol II promoters include regulatable promoters and constitutive promoters. For example, the promoter may be a CMV or RSV promoter. The expression cassette may further contain a polyadenylation signal, such as a synthetic minimal polyadenylation signal. The nucleic acid sequence may further contain a marker gene or stuffer sequences. The expression cassette may be contained in a viral vector. An appropriate viral vector for use in the present invention may be an adenoviral, lentiviral, adeno-associated viral (AAV), poliovirus, herpes simplex virus (HSV) or murine Maloney-based viral vector. The gene of interest may be a gene associated with a condition amenable to siRNA therapy. Examples of such conditions include neurodegenerative diseases, such as a trinucleotide-repeat disease (e.g., polyglutamine repeat disease). Examples of these diseases include Huntington's disease or several spinocerebellar ataxias. Alternatively, the gene of interest may encode a ligand for a chemokine involved in the migration of a cancer cell, or a chemokine receptor.

The present invention also provides an expression cassette containing an isolated nucleic acid sequence encoding a first segment, a second segment located immediately 3' of the first segment, and a third segment located immediately 3' of the second segment, wherein the first and third segments are each less than 30 base pairs in length and each more than 10 base pairs in length, and wherein the sequence of the third segment is the complement of the sequence of the first segment, and wherein the isolated nucleic acid sequence functions as an RNAi molecule targeted against a gene of interest. The expression cassette may be contained in a vector, such as a viral vector.

The present invention provides a method of reducing the expression of a gene product in a cell by contacting a cell with an expression cassette described above. It also provides a method of treating a patient by administering to the patient a composition of the expression cassette described above.

The present invention further provides a method of reducing the expression of a gene product in a cell by contacting a cell with an expression cassette containing an isolated nucleic acid sequence encoding a first segment, a second segment located immediately 3' of the first segment, and a third segment located immediately 3' of the second segment, wherein the first and third segments are each less than 30 base pairs in length and each more than 10 base pairs in length, and wherein the sequence of the third segment is the complement of the sequence of the first segment, and wherein the isolated nucleic acid sequence functions as an RNAi molecule targeted against a gene of interest.

The present method also provides a method of treating a patient, by administering to the patient a composition containing an expression cassette, wherein the expression cassette contains an isolated nucleic acid sequence encoding a first segment, a second segment located immediately 3' of the first segment, and a third segment located immediately 3' of the second segment, wherein the first and third segments are each less than 30 bases in length and each more than 10 bases in length, and wherein the sequence of the third segment is the complement of the sequence of the first segment, and wherein the isolated nucleic acid sequence functions as an RNAi molecule targeted against a gene of interest.

An RNAi molecule may be a "small interfering RNA" or "short interfering RNA" or "siRNA" or "short hairpin RNA" or "shRNA" or "microRNA" or "miRNA." An RNAi molecule an RNA duplex of nucleotides that is targeted to a nucleic acid sequence of interest. As used herein, the term "RNAi molecule" is a generic term that encompasses the subset of shRNAs. A "RNA duplex" refers to the structure formed by the complementary pairing between two regions of a RNA molecule. RNAi molecule is "targeted" to a gene in that the nucleotide sequence of the duplex portion of the RNAi molecule is complementary to a nucleotide sequence of the targeted gene. In certain embodiments, the RNAi molecules are targeted to the sequence encoding Bcl-2. In some embodiments, the length of the duplex of RNAi molecules is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In certain embodiment, the length of the duplex is 19 or 21 base pairs in length. The RNA duplex portion of the RNAi molecule can be part of a hairpin structure. In addition to the duplex portion, the hairpin structure may contain a loop portion positioned between the two sequences that form the duplex. In certain embodiments, the loop is 9 nucleotides in length. The hairpin structure can also contain 3' or 5' overhang portions. In some embodiments, the overhang is a 3' or a 5' overhang 0, 1, 2, 3, 4 or 5 nucleotides in length.

A "small interfering" or "short interfering RNA" or siRNA is a RNA duplex of nucleotides that is targeted to a gene interest. A "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure.

In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length. The "sense" and "antisense" sequences can be attached to the aptamer portion to form aptamer chimeras. As used herein, the term RNAi molecule is meant to be equivalent to other terms used to describe nucleic acid molecules that are capable of mediating sequence specific RNAi, for example, double-stranded RNA (dsRNA), micro-RNA (miRNA), short hairpin RNA (shRNA), short interfering oligonucleotide, short interfering nucleic acid, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetic silencing. In a non-limiting example, modulation of gene expression by siRNA molecules of the invention can result from siRNA mediated cleavage of RNA (either coding or non-coding RNA) via RISC, or alternately, translational inhibition as is known in the art.

The RNAi molecule can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

The RNAi molecule can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

"Knock-down," "knock-down technology" refers to a technique of gene silencing in which the expression of a target gene is reduced as compared to the gene expression prior to the introduction of the RNAi molecule, which can lead to the inhibition of production of the target gene product. The term "reduced" is used herein to indicate that the target gene expression is lowered by 1-100%. In other words, the amount of RNA available for translation into a polypeptide or protein is minimized. For example, the amount of protein may be reduced by 10, 20, 30, 40, 50, 60, 70, 80, 90, 95, or 99%. In some embodiments, the expression is reduced by about 90% (i.e., only about 10% of the amount of protein is observed a cell as compared to a cell where RNAi molecules have not been administered). Knock-down of gene expression can be directed, for example, by the use of dsRNAs, siRNAs or miRNAs.

"RNA interference (RNAi)" is the process of sequence-specific, post-transcriptional gene silencing initiated by an RNAi molecule. During RNAi, RNAi molecules induce degradation of target mRNA with consequent sequence-specific inhibition of gene expression. RNAi involving the use of RNAi molecules has been successfully applied to knockdown the expression of specific genes in plants, *D. melanogaster, C. elegans*, trypanosomes, planaria, hydra, and several vertebrate species including the mouse.

According to a method of the present invention, the expression of Bcl-2 can be modified via RNAi. For example, the accumulation of Bcl-2 can be suppressed in a cell. The term "suppressing" refers to the diminution, reduction or elimination in the number or amount of transcripts present in a particular cell. For example, the accumulation of mRNA encoding Bcl-2 can be suppressed in a cell by RNA interference (RNAi), e.g., the gene is silenced by sequence-specific double-stranded RNA (dsRNA), which is also called short interfering RNA (siRNA). These siRNAs can be two separate RNA molecules that have hybridized together, or they may be a single hairpin wherein two portions of a RNA molecule have hybridized together to form a duplex.

"Recombinant DNA molecule" is a combination of DNA sequences that are joined together using recombinant DNA technology and procedures used to join together DNA sequences as described, for example, in Sambrook and Russell (2001).

The terms "heterologous gene," "heterologous DNA sequence," "exogenous DNA sequence," "heterologous RNA sequence," "exogenous RNA sequence" or "heterologous nucleic acid" each refer to a sequence that either originates from a source foreign to the particular host cell, or is from the same source but is modified from its original or native form. Thus, a heterologous gene in a host cell includes a gene that is endogenous to the particular host cell but has been modified through, for example, the use of DNA shuffling. The terms also include non-naturally occurring multiple copies of a naturally occurring DNA or RNA sequence. Thus, the terms refer to a DNA or RNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA or RNA sequence is a sequence that is naturally associated with a host cell into which it is introduced.

"Genome" refers to the complete genetic material of an organism.

A "vector" is defined to include, inter alia, any viral vector, as well as any plasmid, cosmid, phage or binary vector in double or single stranded linear or circular form that may or may not be self transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional RNA of interest, for example an RNAi molecule. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence. It may constitute an "uninterrupted coding sequence", i.e., lacking an intron, such as in a cDNA, or it may include one or more introns bounded by appropriate splice junctions. An "intron" is a sequence of RNA that is contained in the primary transcript but is removed through cleavage and re-ligation of the RNA within the cell to create the mature mRNA that can be translated into a protein.

The terms "initiation codon" and "termination codon" refer to a unit of three adjacent nucleotides (a 'codon') in a coding sequence that specifies initiation and chain termination, respectively, of protein synthesis (mRNA translation).

"Functional RNA" refers to sense RNA, antisense RNA, ribozyme RNA, siRNA, or other RNA that may not be translated but yet has an effect on at least one cellular process.

The term "RNA transcript" or "transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" are nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Examples of promoters that may be used in the present invention include the mouse U6 RNA promoters, synthetic human H1RNA promoters, SV40, CMV, RSV, RNA polymerase II and RNA polymerase III promoters.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of siRNA constructs, expression may refer to the transcription of the siRNA only. In addition, expression refers to the transcription and stable accumulation of sense (mRNA) or functional RNA. Expression may also refer to the production of protein.

"Altered levels" refers to the level of expression in transgenic cells or organisms that differs from that of normal or untransformed cells or organisms.

"Overexpression" refers to the level of expression in transgenic cells or organisms that exceeds levels of expression in normal or untransformed cells or organisms.

"Antisense inhibition" refers to the production of antisense RNA transcripts capable of suppressing the expression of protein from an endogenous gene or a transgene.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule. An example of a cis-acting sequence on the replicon is the viral replication origin.

The terms "trans-acting sequence" and "trans-acting element" refer to DNA or RNA sequences whose function does not require them to be on the same molecule.

"Chromosomally-integrated" refers to the integration of a foreign gene or nucleic acid construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells.

"Transformed," "transduced," "transgenic" and "recombinant" refer to a host cell into which a heterologous nucleic acid molecule has been introduced. As used herein the term "transfection" refers to the delivery of DNA into eukaryotic (e.g., mammalian) cells. The term "transformation" is used herein to refer to delivery of DNA into prokaryotic (e.g., *E. coli*) cells. The term "transduction" is used herein to refer to infecting cells with viral particles. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

As used herein, the term "derived" or "directed to" with respect to a nucleotide molecule means that the molecule has complementary sequence identity to a particular molecule of interest.

"Treating" as used herein refers to ameliorating at least one symptom of, curing and/or preventing the development of a disease or a condition.

Expression Cassettes of the Invention

To prepare expression cassettes, the recombinant DNA sequence or segment may be circular or linear, double-stranded or single-stranded. Generally, the DNA sequence or segment is in the form of chimeric DNA, such as plasmid DNA or a vector that can also contain coding regions flanked by control sequences that promote the expression of the recombinant DNA present in the resultant transformed cell.

Aside from recombinant DNA sequences that serve as transcription units for an RNA transcript, or portions thereof, a portion of the recombinant DNA may be untranscribed, serving a regulatory or a structural function. For example, the recombinant DNA may have a promoter that is active in mammalian cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the siRNA, or the like. Such elements may be included in the DNA as desired to obtain the optimal performance of the siRNA in the cell.

Control sequences are DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Operably linked nucleic acids are nucleic acids placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked DNA sequences are DNA sequences that are linked are contiguous. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells may contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. For example, reporter genes include the chloramphenicol acetyl transferase gene (cat) from Tn9 of *E. coli* and the luciferase gene from firefly *Photinus pyralis*. Expression of the reporter gene is assayed at a suitable time after the DNA has been introduced into the recipient cells.

The general methods for constructing recombinant DNA that can transfect target cells are well known to those skilled in the art, and the same compositions and methods of construction may be utilized to produce the DNA useful herein.

The recombinant DNA can be readily introduced into the host cells, e.g., mammalian, bacterial, yeast or insect cells by transfection with an expression vector composed of DNA encoding the siRNA by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. For mammalian gene therapy, as described herein below, it is desirable to use an efficient means of inserting a copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like.

As discussed above, a "transfected" or "transduced" host cell or cell line is one in which the genome has been altered or augmented by the presence of at least one heterologous or recombinant nucleic acid sequence. The host cells of the present invention are typically produced by transfection with a DNA sequence in a plasmid expression vector, a viral expression vector, or as an isolated linear DNA sequence. The transfected DNA can become a chromosomally integrated recombinant DNA sequence, which is composed of sequence encoding the siRNA.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the host cell.

According to one embodiment, the cells are transfected or transduced or otherwise genetically modified in vivo. The cells from the mammalian recipient are transduced or transfected in vivo with a vector containing exogenous nucleic acid material for expressing a heterologous (e.g., recombinant) gene encoding a therapeutic agent and the therapeutic agent is delivered in situ.

Methods for Introducing the Expression Cassettes of the Invention into Cells

The condition amenable to gene inhibition therapy may be a prophylactic process, i.e., a process for preventing disease or an undesired medical condition. Thus, the instant invention embraces a system for delivering siRNA that has a prophylactic function (i.e., a prophylactic agent) to the mammalian recipient.

The inhibitory nucleic acid material (e.g., an expression cassette encoding siRNA directed to a gene of interest) can be introduced into the cell ex vivo or in vivo by genetic transfer methods, such as transfection or transduction, to provide a genetically modified cell. Various expression vectors (i.e., vehicles for facilitating delivery of exogenous nucleic acid into a target cell) are known to one of ordinary skill in the art.

As used herein, "transfection of cells" refers to the acquisition by a cell of new nucleic acid material by incorporation of added DNA. Thus, transfection refers to the insertion of nucleic acid into a cell using physical or chemical methods. Several transfection techniques are known to those of ordinary skill in the art including calcium phosphate DNA co-precipitation, DEAE-dextran, electroporation, cationic liposome-mediated transfection, tungsten particle-facilitated microparticle bombardment, and strontium phosphate DNA co-precipitation.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous nucleic acid material contained within the retrovirus is incorporated into the genome of the transduced cell. A cell that has been transduced with a chimeric DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

The exogenous nucleic acid material can include the nucleic acid encoding the siRNA together with a promoter to control transcription. The promoter characteristically has a specific nucleotide sequence necessary to initiate transcription. The exogenous nucleic acid material may further include additional sequences (i.e., enhancers) required to obtain the desired gene transcription activity. For the purpose of this discussion an "enhancer" is simply any non-translated DNA sequence that works with the coding sequence (in cis) to change the basal transcription level dictated by the promoter. The exogenous nucleic acid material may be introduced into the cell genome immediately downstream from the promoter so that the promoter and coding sequence are operatively linked so as to permit transcription of the coding sequence. An expression vector can include an exogenous promoter element to control transcription of the inserted exogenous gene. Such exogenous promoters include both constitutive and regulatable promoters.

Naturally-occurring constitutive promoters control the expression of essential cell functions. As a result, a nucleic acid sequence under the control of a constitutive promoter is expressed under all conditions of cell growth. Constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the beta-actin promoter, and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others.

Nucleic acid sequences that are under the control of regulatable promoters are expressed only or to a greater or lesser degree in the presence of an inducing or repressing agent, (e.g., transcription under control of the metallothionein promoter is greatly increased in presence of certain metal ions). Regulatable promoters include responsive elements (REs) that stimulate transcription when their inducing factors are bound. For example, there are REs for serum factors, steroid hormones, retinoic acid, cyclic AMP, and tetracycline and doxycycline. Promoters containing a particular RE can be chosen in order to obtain an regulatable response and in some cases, the RE itself may be attached to a different promoter, thereby conferring regulatability to the encoded nucleic acid sequence. Thus, by selecting the appropriate promoter (constitutive versus regulatable; strong versus weak), it is possible to control both the existence and level of expression of a nucleic acid sequence in the genetically modified cell. If the nucleic acid sequence is under the control of an regulatable promoter, delivery of the therapeutic agent in situ is triggered by exposing the genetically modified cell in situ to conditions for permitting transcription of the nucleic acid sequence, e.g., by intraperitoneal injection of specific inducers of the regulatable promoters which control transcription of the agent. For example, in situ expression of a nucleic acid sequence under the control of the metallothionein promoter in genetically modified cells is enhanced by contacting the genetically modified cells with a solution containing the appropriate (i.e., inducing) metal ions in situ.

Accordingly, the amount of siRNA generated in situ is regulated by controlling such factors as the nature of the promoter used to direct transcription of the nucleic acid sequence, (i.e., whether the promoter is constitutive or regulatable, strong or weak) and the number of copies of the exogenous nucleic acid sequence encoding a siRNA sequence that are in the cell.

In one embodiment of the present invention, an expression cassette may contain a pol II promoter that is operably linked to a nucleic acid sequence encoding a siRNA. Thus, the pol II promoter, i.e., a RNA polymerase II dependent promoter, initiates the transcription of the siRNA. In another embodiment, the pol II promoter is regulatable.

A pol II promoter may be used in its entirety, or a portion or fragment of the promoter sequence may be used in which the portion maintains the promoter activity. As discussed herein, pol II promoters are known to a skilled person in the art and include the promoter of any protein-encoding gene, e.g., an endogenously regulated gene or a constitutively expressed gene. For example, the promoters of genes regulated by cellular physiological events, e.g., heat shock, oxygen levels and/or carbon monoxide levels, e.g., in hypoxia, may be used in the expression cassettes of the invention. In addition, the promoter of any gene regulated by the presence of a pharmacological agent, e.g., tetracycline and derivatives thereof, as well as heavy metal ions and hormones may be employed in the expression cassettes of the invention. In an embodiment of the invention, the pol II promoter can be the CMV promoter or the RSV promoter. In another embodiment, the pol II promoter is the CMV promoter.

As discussed above, a pol II promoter of the invention may be one naturally associated with an endogenously regulated gene or sequence, as may be obtained by isolating the 5' non-coding sequences located upstream of the coding segment and/or exon. The pol II promoter of the expression cassette can be, for example, the same pol II promoter driving expression of the targeted gene of interest. Alternatively, the nucleic acid sequence encoding the RNAi molecule may be placed under the control of a recombinant or heterologous pol II promoter, which refers to a promoter that is not normally associated with the targeted gene's natural environment. Such promoters include promoters isolated from any eukaryotic cell, and promoters not "naturally occurring," i.e., containing different elements of different transcriptional regulatory regions, and/or mutations that alter expression. In addition to producing nucleic acid sequences of promoters synthetically, sequences may be produced using recombinant cloning and/or nucleic acid amplification technology, including PCR, in connection with the compositions disclosed herein.

In one embodiment, a pol II promoter that effectively directs the expression of the siRNA in the cell type, organelle, and organism chosen for expression will be employed. Those of ordinary skill in the art of molecular biology generally know the use of promoters for protein expression. The promoters employed may be constitutive, tissue-specific, inducible, and/or useful under the appropriate conditions to direct high level expression of the introduced DNA segment, such as is advantageous in the large-scale production of recombinant proteins and/or peptides. The identity of tissue-specific promoters, as well as assays to characterize their activity, is well known to those of ordinary skill in the art.

In addition to at least one promoter and at least one heterologous nucleic acid sequence encoding the siRNA, the expression vector may include a selection gene, for example, a neomycin resistance gene, for facilitating selection of cells that have been transfected or transduced with the expression vector.

Cells can also be transfected with two or more expression vectors, at least one vector containing the nucleic acid sequence(s) encoding the siRNA(s), the other vector containing a selection gene. The selection of a suitable promoter, enhancer, selection gene and/or signal sequence is deemed to be within the scope of one of ordinary skill in the art without undue experimentation.

The following discussion is directed to various utilities of the instant invention. For example, the instant invention has utility as an expression system suitable for silencing the expression of gene(s) of interest.

The instant invention also provides methods for genetically modifying cells of a mammalian recipient in vivo. According to one embodiment, the method comprises introducing an expression vector for expressing a siRNA sequence in cells of the mammalian recipient in situ by, for example, injecting the vector into the recipient.

Thus, as will be apparent to one of ordinary skill in the art, a variety of suitable viral expression vectors are available for transferring exogenous nucleic acid material into cells. The selection of an appropriate expression vector to express a therapeutic agent for a particular condition amenable to gene silencing therapy and the optimization of the conditions for insertion of the selected expression vector into the cell, are within the scope of one of ordinary skill in the art without the need for undue experimentation.

In another embodiment, the expression vector is in the form of a plasmid, which is transferred into the target cells by one of a variety of methods: physical (e.g., microinjection, electroporation, scrape loading, microparticle bombardment) or by cellular uptake as a chemical complex (e.g., calcium or strontium co-precipitation, complexation with lipid, complexation with ligand). Several commercial products are available for cationic liposome complexation including Lipofectin™ (Gibco-BRL, Gaithersburg, Md.) and Transfectam™ (ProMega, Madison, Wis.). However, the efficiency of transfection by these methods is highly dependent on the nature of the target cell and accordingly, the conditions for optimal transfection of nucleic acids into cells using the above-mentioned procedures must be optimized. Such optimization is within the scope of one of ordinary skill in the art without the need for undue experimentation.

Diseases and Conditions Amendable to the Methods of the Invention

In the certain embodiments of the present invention, a mammalian recipient to an expression cassette of the invention has a condition that is amenable to gene silencing therapy. As used herein, "gene silencing therapy" refers to administration to the recipient exogenous nucleic acid material encoding a therapeutic siRNA and subsequent expression of the administered nucleic acid material in situ. Thus, the phrase "condition amenable to siRNA therapy" embraces conditions such as genetic diseases (i.e., a disease condition that is attributable to one or more gene defects), acquired pathologies (i.e., a pathological condition that is not attributable to an inborn defect), cancers, neurodegenerative diseases, e.g., trinucleotide repeat disorders, and prophylactic processes (i.e., prevention of a disease or of an undesired medical condition). A gene "associated with a condition" is a gene that is either the cause, or is part of the cause, of the condition to be treated. Examples of such genes include genes associated with a neurodegenerative disease (e.g., a trinucleotide-repeat disease such as a disease associated with polyglutamine repeats, Huntington's disease, and several spinocerebellar ataxias), and genes encoding ligands for chemokines involved in the migration of a cancer cells, or chemokine receptor. Also siRNA expressed from viral vectors may be used for in vivo antiviral therapy using the vector systems described.

Accordingly, as used herein, the term "therapeutic siRNA" refers to any siRNA that has a beneficial effect on the recipient. Thus, "therapeutic siRNA" embraces both therapeutic and prophylactic siRNA.

Differences between alleles that are amenable to targeting by siRNA include disease-causing mutations as well as polymorphisms that are not themselves mutations, but may be linked to a mutation or associated with a predisposition to a disease state.

A condition amenable to gene silencing therapy can be a genetic disorder or an acquired pathology that is manifested by abnormal cell proliferation, e.g., cancer. According to this embodiment, the instant invention is useful for silencing a gene involved in neoplastic activity. The present invention can also be used to inhibit overexpression of one or several genes. The present invention can be used to treat neuroblastoma, medulloblastoma, or glioblastoma.

Dosages, Formulations and Routes of Administration of the Agents of the Invention The agents of the invention are preferably administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems, which are well known to the art.

Administration of the aptamer chimera may be accomplished through the administration of the nucleic acid molecule. Pharmaceutical formulations, dosages and routes of administration for nucleic acids are generally known in the art.

The present invention envisions treating a disease, for example, cancer, in a mammal by the administration of an agent, e.g., a nucleic acid composition, an expression vector, or a viral particle of the invention. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation), can be administered by a variety of routes including parenteral, including by intravenous and intramuscular routes, as well as by direct injection into the diseased tissue. For example, the therapeutic agent may be directly injected into the cancer. In another example, the therapeutic agent may be introduced intramuscularly for viruses that traffic back to affected neurons from muscle, such as AAV, lentivirus and adenovirus. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules, as a solution, a suspension or an emulsion.

Pharmaceutical formulations containing the therapeutic agents of the invention can be prepared by procedures known in the art using well known and readily available ingredients.

The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0, saline solutions, and water.

Example 1

HER2 RNA Aptamers for Targeted Delivery

Figure 5:
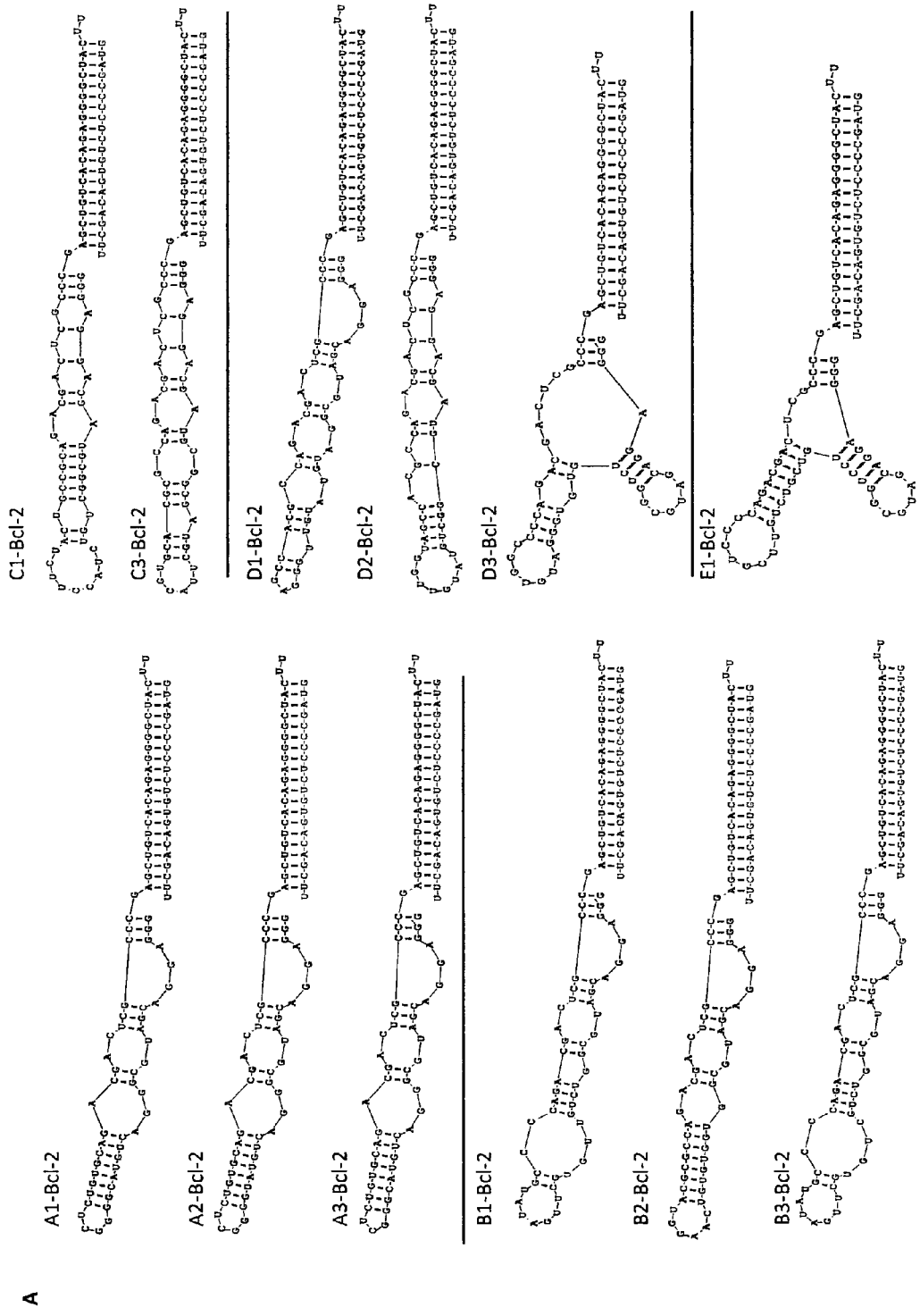
Figure 5:
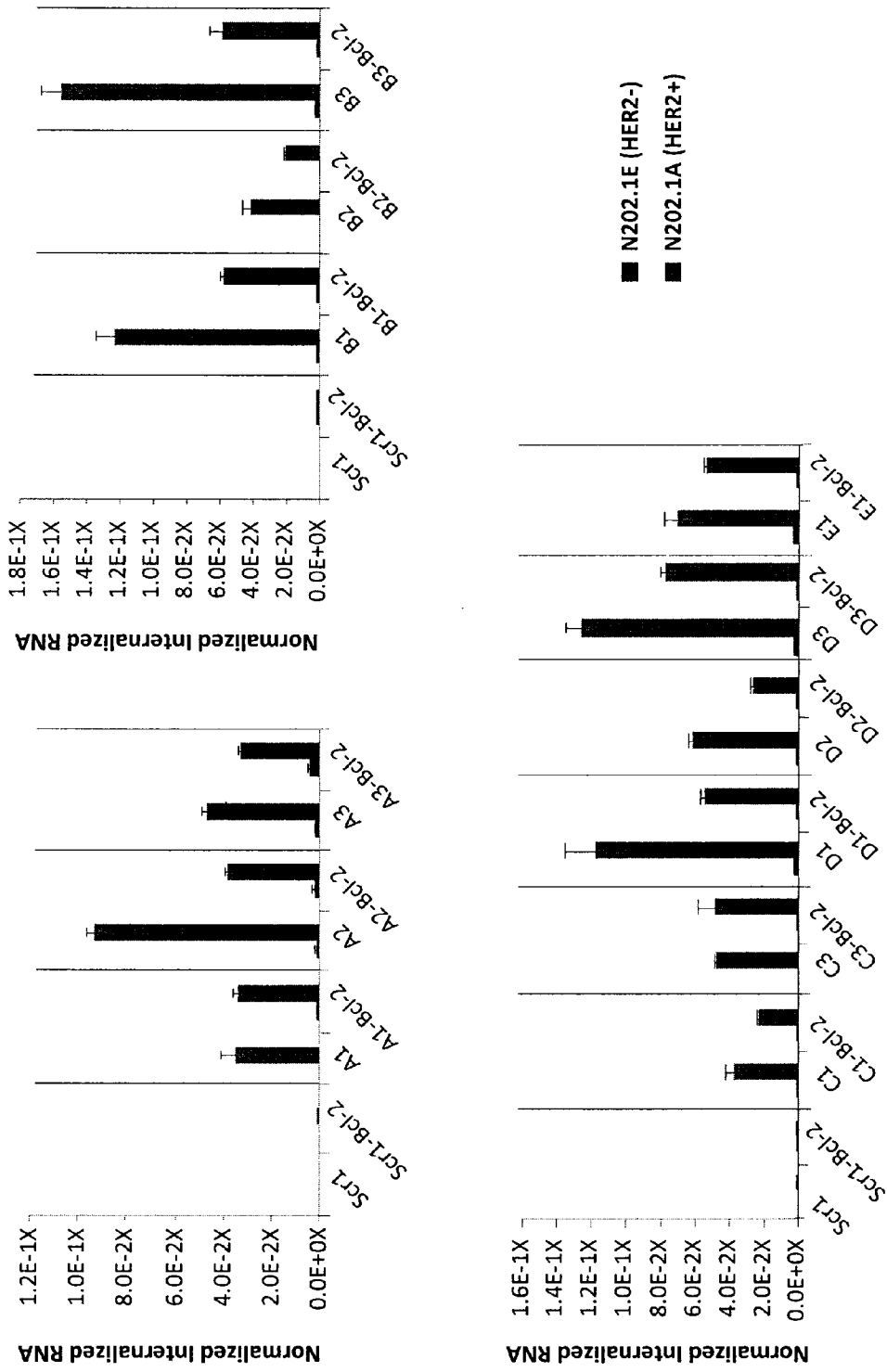
Figure 5:
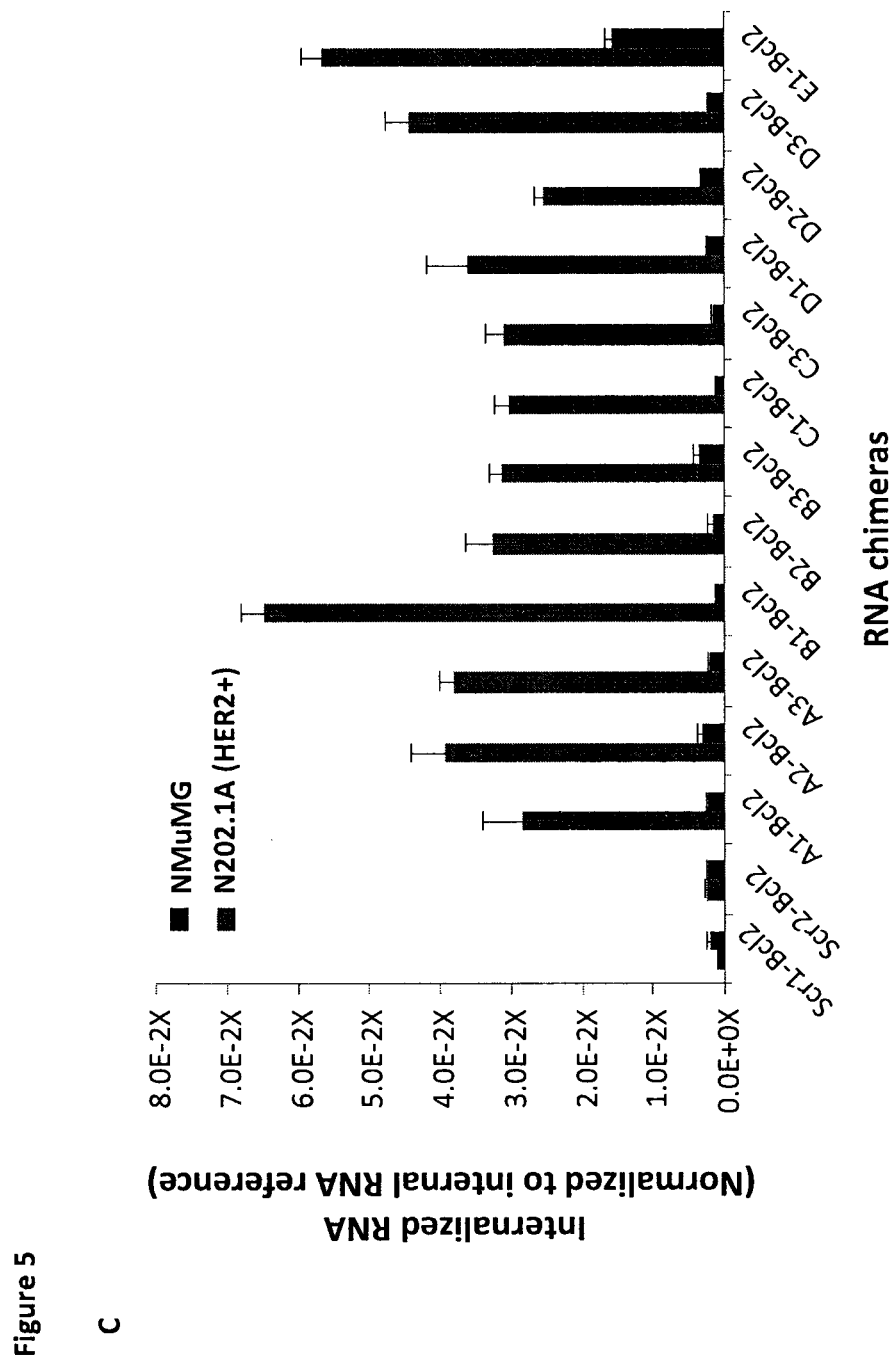
Figure 5:
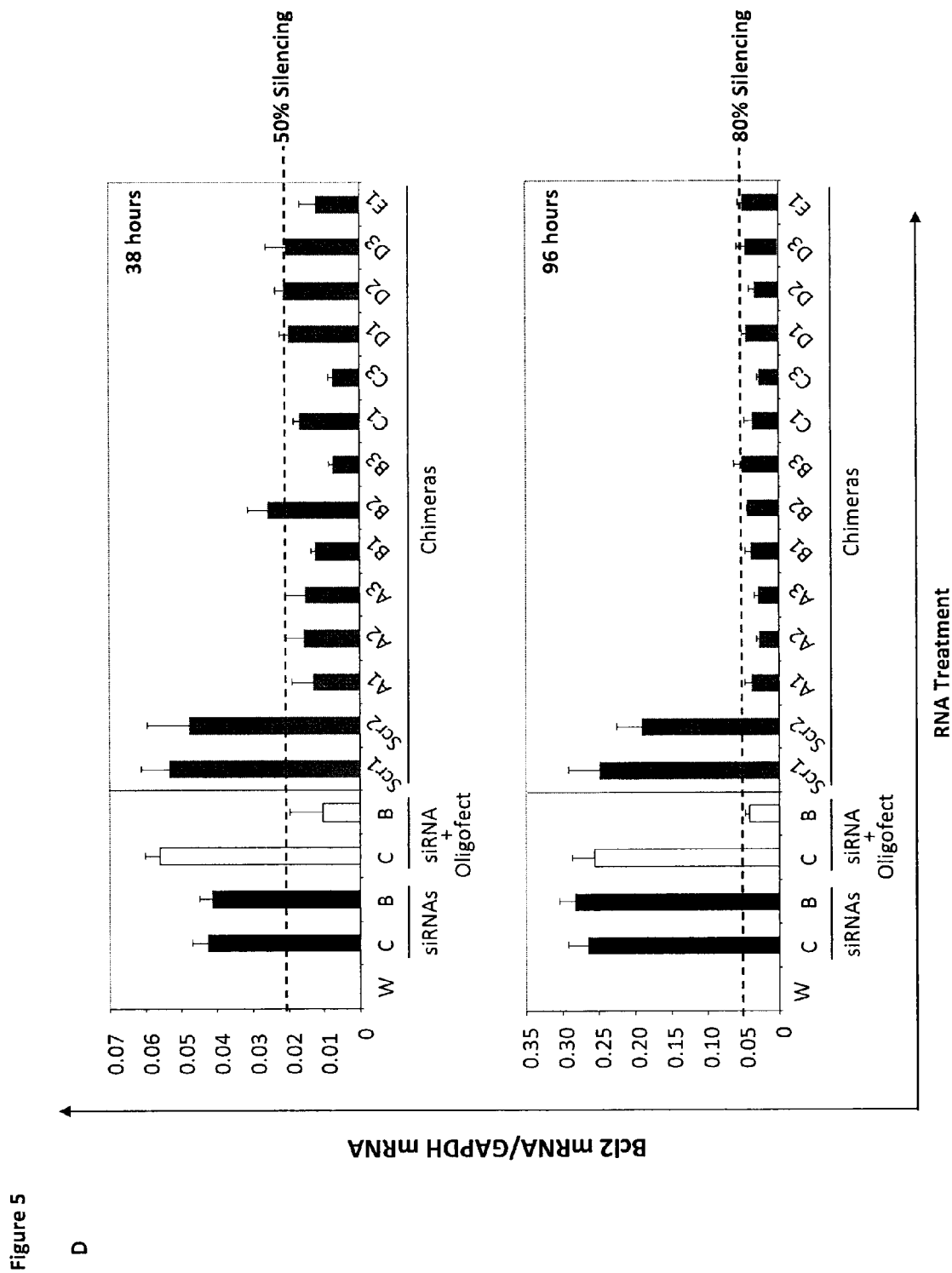
Figure 5:
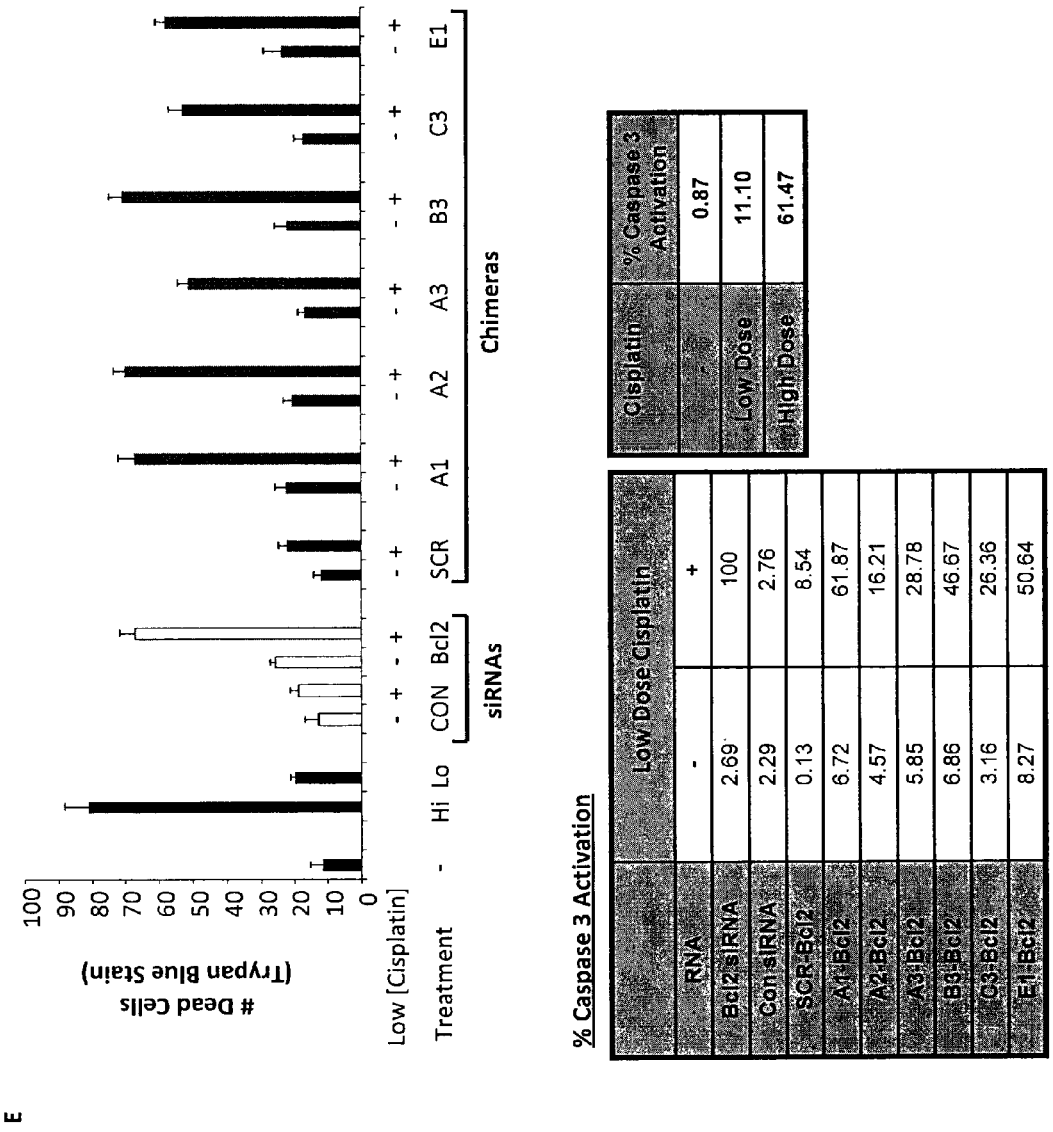

The inventors have modified the standard SELEX (systematic evolution of ligands by exponential enrichment) methodology to enable the rapid isolation of aptamers for siRNA delivery that selectively internalize into target cells (FIG. 1A). Using the cell-internalization SELEX approach the inventors enriched for RNA sequences that selectively internalize into HER2-positive breast cancer cells (FIGS. 1C and 2C-E). These RNAs are useful for targeting therapeutics (e.g. siRNAs, chemotherapy, radiotherapy) directly to breast cancer cells expressing HER2 thereby reducing global toxicity. Towards this end, the inventors conjugated those aptamers with the greatest specificity and internalization potential to siRNAs targeting pro-survival genes (FIG. 5). While most of the aptamer-siRNA chimeras showed increased internalization into HER2-expressing cells, as compared to cells lacking HER2 expression, the following chimeras were particularly effective: A1-Bcl2, A2-Bcl2, A3-Bcl2, B1-Bcl2, B3-Bcl2, C1-Bcl2, C3-Bcl2, D1-Bcl2, D2-Bcl2, and D3-Bcl2. Furthermore, the inventors demonstrate that silencing of the one of these genes (Bcl2) sensitized HER2-expressing breast cancer cells to chemotherapy (e.g., cisplatin treatment) (FIG. 5E).

The current treatment for HER2-positive tumors is Herceptin, an antibody-based inhibitor of HER2 activity. While this antibody shows some growth inhibitory effects, women treated with Herceptin develop resistance to the therapy, highlighting the need for novel, more efficient targeted therapies. The advances described herein results in novel cancer therapeutics that have an important impact for treating breast cancer patients (with HER2-positive status), including patients with refractory disease, and patients with other HER2-expressing cancers.

Figure 6:
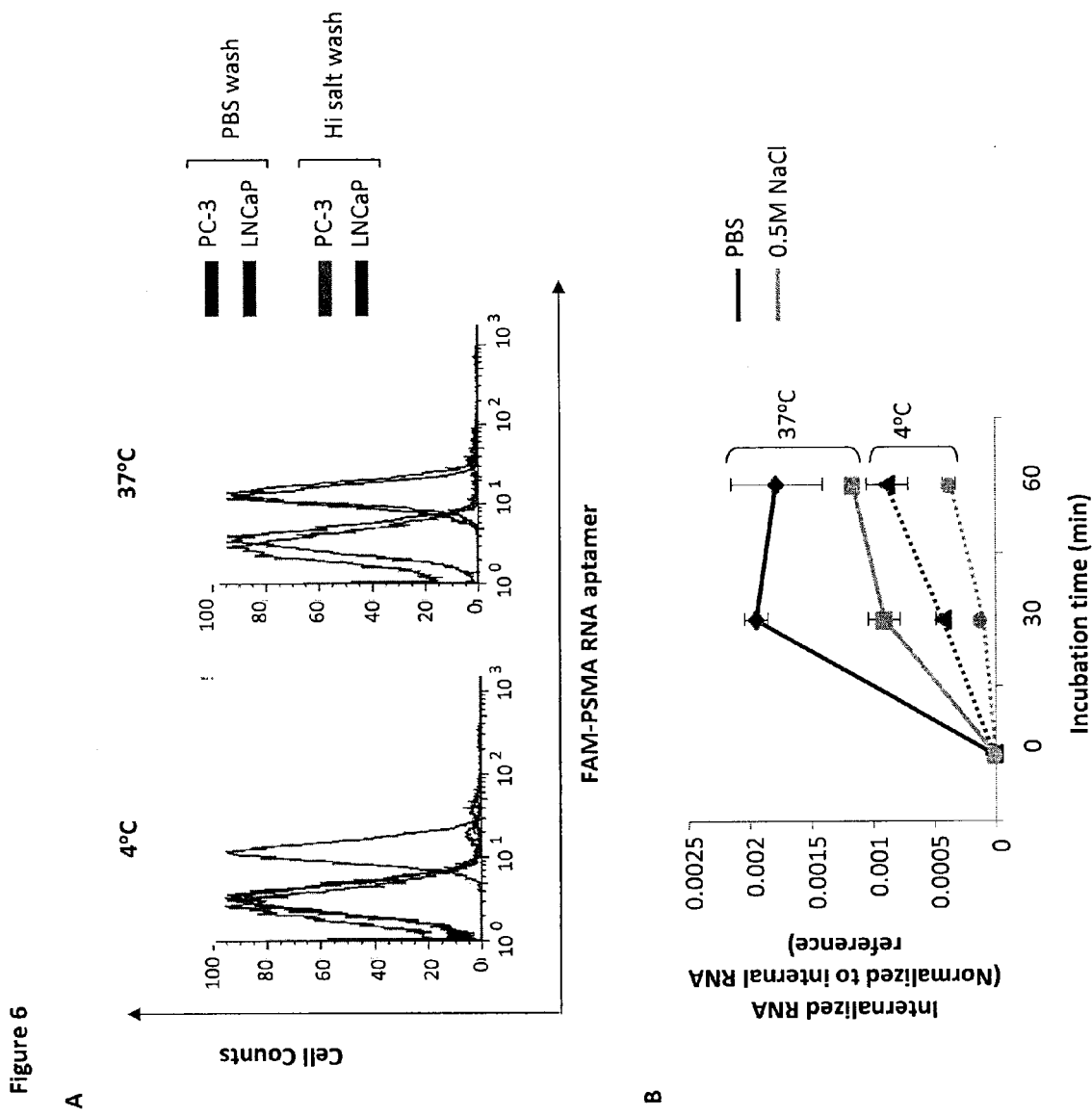

The inventors describe a novel, cell-based SELEX approach for isolating RNA aptamers that selectively internalize into target cells (FIG. 1A). The proof-of-concept for this approach is demonstrated using mouse mammary carcinoma cells expressing high levels of rat HER2 on the cell surface (target cell) (FIG. 1B). The inventors demonstrated that after several rounds of positive (against target cells) and negative (against cells lacking HER2) selection, they were able to enrich for RNA pools that preferentially internalize into HER2-positive cells (target cells) (FIG. 1C). To ensure that they were looking only at internalized material, they performed a stringent salt wash (0.5 M NaCl) to remove any RNA bound to the surface of the cells (FIG. 6). High-throughput 454 sequencing was employed to identify individual RNA sequences from the later rounds of selection (Rounds 6, 7, 8) (FIG. 2A). The inventors demonstrated that the individual RNA aptamers retain the ability to selectively internalize into HER2-expressing cells (N202.1A and 85819) as compared to cells lacking HER2-expression (N202.1E and 78717) (FIG. 2C, 2D) using qRT-PCR as wells as flow cytometry (FIG. 2E). In addition, the inventors showed that the HER2-aptamers selectively internalize into HER2-overexpressing mammary cancer cells but not normal mammry epithelial cells which express low-to-no HER2 on the cell surface (FIG. 7). Together the above results suggest that the novel cell-based internalization SELEX approach was successfully employed to identify RNA aptamers that selectively internalize into target therapeutic cells and thus minimize targeting of normal (non-target cells).

The inventors next verified that several of the internalizing aptamers were binding specifically to HER2 using fluorescence polarization (FP). This was done by measuring binding of the RNAs to recombinant purified rat HER2-ECD (extra cellular domain) (FIG. 3). This experiment clearly demonstrates that aptamers A2, B1, C1, D1, and E1 bind to rat HER2. A control protein (human glyoxylase) was used as a negative control for binding in these studies.

The anti-apoptotic factor, Bcl2 is often overexpressed in many human cancers. In many of these cancers, Bcl2 expression correlates with HER2 expression, suggesting that HER2 cancers might upregulate Bcl2 as a way of promoting survival of the cancer cell. The inventors investigated whether Bcl2 expression was indeed elevated in the HER2 expressing mammary carcinoma cells (N202.1A and 85819). They showed that Bcl2 is indeed upregulated in the HER2-expressing cells compared to HER2-negative cells both at the RNA (FIG. 4A, left panel) and protein levels (FIG. 4B, right panel and FIG. 8). These finding suggest that Bcl2 may be involved in promoting survival of these cancer cells and possibly resistance to cytotoxic agents. In order to silence Bcl2 expression in these cells, the inventors identified a siRNA specific for Bcl2 (Oakes, S A et al., PNAS 2005) and showed that this siRNA can silence Bcl2 expression in these cells (FIG. 4B). It is important to note that the inventors showed that silencing Bcl2 expression in HER2-positive mammary cancer cells sensitized these cells to chemotherapy (cisplatin treatment) (FIG. 4C).

The inventors next delivered the Bcl2 siRNA to HER2-positive cells by covalently conjugating the siRNA to the HER2RNA aptamers. A total of 12 different HER2 aptamers-Bcl2 siRNA chimeras were engineered (A1-Bcl2, A2-Bcl2, A3-Bcl2, B1-Bcl2, B2-Bcl2, B3-Bcl2, C1-Bcl2, C3-Bcl2, D1-Bcl2, D2-Bcl2, D3-Bcl2, E1-Bcl2) (FIG. 5A). The inventors demonstrated the ability of these aptamer-siRNA chimeras to internalize into HER2-positive (N202.1A) as compared to HER2-negative (N202.1E) mammary cancer cells using qRT-PCR, suggesting that appending the siRNA onto the aptamer does not affect the aptamers ability to 1) bind to HER2 on the cell surface and 2) internalize upon binding (FIG. 5B). The inventors confirmed specificity of targeting by showing that the aptamer-siRNA chimeras internalize into 85819 (HER-2 positive) but not 78717 (HER2 negative) mammary carcinoma cells that also express rat HER2 (FIG. 9). In addition, they confirmed that the chimeras internalize specifically into cancer cells expressing high levels of HER2 on the surface but not normal mammary epithelial cells which express low-to-no HER2 on the cell surface (FIG. 5C). These data demonstrate the target specificity of these aptamer-siRNA chimeras. An important observation was that upon internalization into the HER2-positive cells, the aptamer-siRNA chimeras lead to robust silencing of Bcl2 gene expression as measured by qRT-PCR (FIG. 5D). Aptamer-siRNA chimera-mediated silencing was assessed at 38 h (FIG. 5D, top panel) and 96 h (FIG. 5D, bottom, panel) following incubation (in the absence of transfection reagent) with the different chimeras. Silencing of Bcl2 gene expression ranged from 50-80% at the 38 h time point and between 10-20% at the 96 h time point. Because the Bcl2-siRNA sensitizes HER2-positive cancer cells to chemotherapy treatment (cisplatin), the inventors next asked whether the Bcl2 siRNA in the context of the chimeras was also capable of sensitizing HER2-positive (N202.1A) cells to cisplatin treatment. The data in FIG. 5E demonstrate that several of the chimeras tested (A1-Bcl2, A2-Bcl2, A3-Bcl2, B3-Bcl2, C3-Bcl2, and E1-Bcl2) lead to an increased sensitization of HER2-positive cells to cisplatin treatment. It is important to note that because the Bcl2 siRNA is predominantly targeted to HER2-overexpressing cancer cells, it is likely to reduce any of-target effect of the siRNA in normal (non-target) cells. Furthermore, targeting of the siRNAs to the appropriate cell population is likely to reduce the amount of material (siRNA) need of the intended therapeutic effect.

In summary, the inventors have identified and characterized chemically modified RNA oligonucleotides that internalized specifically into HER2-expressing cells (FIG. 2C-E). These siRNAs were conjugated to an siRNA to Bcl-2 (an oncogene/proapoptotic gene) overexpressed in many human malignancies and retained their ability to internalize into HER2-expressing cells (FIG. 5B). The inventors verified that these RNA conjugates did not internalize into normal mammary epithelial cells (NMuMG) that may express very low levels of HER2 (FIG. 5C). When the HER2 aptamer-Bcl2 siRNA conjugates are added to cells (in the absence of a transfection reagent) the inventors observed silencing of the siRNA target gene (in this case Bcl2) (FIG. 5D) and sensitization of the HER2-positive cancer cells to the chemotherapeutic agent cisplatin (FIG. 5E).

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An aptamer molecule not more than 55 nucleotides in length comprising the nucleic acid sequence 5'-GGGAGGACGAUGCGG-R$^1$-CAGACGACUCGCCCGA-3' (SEQ ID NO: 45), wherein R$^1$ is

GACUGUACGGGGCUCUGUG, (A1, SEQ ID NO: 1)

GACUGUAUGGGGCUCUGUG, (A2, SEQ ID NO: 2)

GACUGUACGGGCUCUGUG, (A3, SEQ ID NO: 3)

UCUCAGUAGUGGGCCUGCUG, (A4, SEQ ID NO: 4)

GACUGUAUGGGCUCUGUG, (A5, SEQ ID NO: 5)

GACUGUAUCGGGGCUCUGUG, (A6, SEQ ID NO: 6)

GACUGUAYGGGGCUCUGUG, (A-consensus, SEQ ID NO: 7)

AUGUAUGUUGGGAGCCACGC, (D1, SEQ ID NO: 8)

CUGUAUGUUGGUAGCCACGC, (D2, SEQ ID NO: 9)

UCUGUGUGGGAUGUGGCCC, (D3, SEQ ID NO: 10)

AUGUAUGUUGGGAGCCACGC, (D-consensus, SEQ ID NO: 11)

UCUGUUGUGCUUGAUAUGCCC, (B1, SEQ ID NO: 12)

UGGUGUGUCAAGGUACGCGC, (B2, SEQ ID NO: 13)

UCUGCUGUGCUUGAUAUGCCC, (B3, SEQ ID NO: 14)

UCUGUUGUGCUUGAUAUGCCC, (B-consensus, SEQ ID NO: 15)

CUGUCUACCUUCUACUGCCG, (C1, SEQ ID NO: 16)

CCAGUUUACCUUACACUCGC, (C2, SEQ ID NO: 17)

CGAUGCUUACGUGCACGCGC, (C3, SEQ ID NO: 18)

CUGUCUACCUUCUACUGCCC, (C4, SEQ ID NO: 19)

UUGUCUACCUUCUACUGCCG, (C5, SEQ ID NO: 20)

CUGUCUWMGCUUCUACUGCCG, (C-consensus, SEQ ID NO: 21)

UCCUGUCGUCUGUUCGUCCC, (E1, SEQ ID NO: 22)

CCGUGUCGUCUGUACUGCCC, (E2, SEQ ID NO: 23)

or

UCCUGUCGUYUGKUCSKCCC. (E-consensus, SEQ ID NO: 24)

2. The aptamer of claim 1, wherein the nucleic acid molecule comprises nucleic acid 5'-GGGAGGACGAUGCGG-GACUGUAYGGGGCUCUGUGCAGAC-GACUCGCCCGA-3' (SEQ ID NO: 25); 5'-GGGAGGACGAUGCGGUCUGUUGUGCU-UGAUAUGCCCCAGACGACUCGCCCGA-3' (SEQ ID NO: 26); 5'-GGGAGGACGAUGCGGCUGUCUWMGCU-UCUACUGCCGCAGACGACUCGCCCGA-3' (SEQ ID NO: 27); 5'-GGGAGGACGAUGCGGAUGUAUGUUGG-GAGCCACGCCAGACGACUCGCCCGA-3' (SEQ ID NO: 28); or 5'-GGGAGGACGAUGCGGUCCUGUCGUYU-GKUCSKCCCCAGACGACUCGCCCGA-3' (SEQ ID NO: 29).

3. A conjugate comprising the aptamer of claim 1 operably linked to a Bcl-2 RNAi molecule.

4. The conjugate of claim 3, wherein the Bcl-2 RNAi molecule comprises nucleic acid 5'-GCUGUCACA-GAGGGGCUACUU-3' (SEQ ID NO: 30).

5. The conjugate of claim 4, consisting of 5'-GGGAG-GACGAAUGCGGGACUGUACGGGGCUCU- GUGCAGACGACUCGCCCGAGCUGUCACA-GAGGGGCUACUU-3' (A1-Bcl-2, SEQ ID NO:32); 5'-GGGAGGACGAUGCGGGACU-GUAUGGGGCUCUGUGCAGACGACUCGC-CCGAGCUGUCACAGAGGGGCUACUU-3' (A2-Bcl-2, SEQ ID NO:33); 5'-GGGAGGACGAUGCGGGACU-GUACGGGCUCUGUGCAGACGACUCGC-CCGAGCUGUCACAGAGGGGCUACUU-3' (A3-Bcl-2, SEQ ID NO:34); 5'-GGGAGGACGAUGCGGUCUGUU-GUGCUUGAUAUGCCCCAGACGACUCGC-CCGAGCUGUCACAGAGGGGCUACUU-3' (B1-Bcl-2, SEQ ID NO:35); 5'-GGGAGGACGAUGCGGUGGUGU-GUCAAGGUACGCGCCAGACGACUCGC-CCGAGCUGUCACAGAGGGGCUACUU-3' (B2-Bcl-2, SEQ ID NO:36); 5'-GGGAGGACGAUGCGGUCUGCU-GUGCUUGAUAUGCCCCAGACGACUCGC-CCGAGCUGUCACAGAGGGGCUACUU-3' (B3-Bcl-2, SEQ ID NO:37); 5'-GGGAGGACGAUGCGGCUGUC-UACCUUCUACUGCCGCAGACGACUCGC-CCGAGCUGUCACAGAGGGGCUACUU-3' (C1-Bcl-2, SEQ ID NO:38); 5'-GGGAGGACGAUGCGGCGAUGCU-UACGUGCACGCGCCAGACGAACUCGC-CCGAGCUGUCACAGAGGGGCUACUU-3' (C2-Bcl-2, SEQ ID NO:39); 5'-GGGAGGACGAUGCGGCGAUGCU-UACGUGCACGCGCCAGACGACUCGC-CCGAGCUGUCACAGAGGGGCUACUU-3' (C3-Bcl-2, SEQ ID NO:40); 5'-GGGAGGACGAUGCGGAUGUAUG-UUGGGAGCCACGCCAGACGACUCGC-CCGAGCUGUCACAGAGGGGCUACUU-3' (D1-Bcl-2, SEQ ID NO:41); 5'-GGGAGGACGAUGCGGCUGUAUG-UUGGUAGCCACGCCAGACGACUCGC-CCGAGCUGUCACAGAGGGGCUACUU-3' (D2-Bcl-2, SEQ ID NO:42); 5'-GGGAGGACGAUGCGGUCUGU-GUGGGAUGUGGCCCCAGACGACUCGC-CCGAGCUGUCACAGAGGGGCUACUU-3' (D3-Bcl-2, SEQ ID NO:43); or 5'-GGGAGGACGAUGCGGUCCU-GUCGUCUGUUCGUCCCAGACGACUCGC-CCGAGCUGUCACAGAGGGGCUACUU-3' (E1-Bcl-2, SEQ ID NO:44).

6. The conjugate of claim 4 hybridized to 5'-GUAGC-CCCUCUGUGACAGCUU-3' (SEQ ID NO:31).

7. A complex comprising the aptamer of claim 1 linked to a therapeutic or diagnostic molecule.

8. The complex of claim 7, wherein the aptamer is linked to a therapeutic molecule, and the therapeutic molecule is a siRNA molecule.

9. The complex of claim 8, wherein the siRNA has a guide strand and a passenger strand, and wherein the guide strand is linked to the nucleic acid molecule.

10. The complex of claim 7, which further comprises a PEG molecule.

11. The complex of claim 10, wherein the PEG molecule has an average molecular weight of about 10 to 100 kDa in size.

12. A nucleic acid molecule encoding the aptamer of claim 1.

13. An expression cassette comprising the molecule of claim 12.

14. The expression cassette of claim 13, further comprising a promoter.

15. A viral vector comprising the expression cassette of claim 13.

16. A pharmaceutical composition comprising the aptamer of claim 1.

17. A method for delivering a therapeutic or diagnostic molecule to a cell having a HER2 receptor, comprising contacting the cell with the aptamer of claim 1.

18. A method for treating a patient having cancer comprising administering the aptamer of claim 1 to the patient.

19. The method of claim 18, further comprising administering Herceptin.

* * * * *

```
                              SEQUENCE LISTING

<160> NUMBER OF SEQ ID NOS: 45

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gacuguacgg ggcucugug                                                      19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
gacuguaugg ggcucugug                                                      19

<210> SEQ ID NO 3
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gacuguacgg gcucugug                                                       18

<210> SEQ ID NO 4
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 4
ucucaguagu gggccugcug                                              20

<210> SEQ ID NO 5
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gacuguaugg gcucugug                                                18

<210> SEQ ID NO 6
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gacuguaucg gggcucugug                                              20

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gacuguaygg ggcucugug                                               19

<210> SEQ ID NO 8
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
auguauguug ggagccacgc                                              20

<210> SEQ ID NO 9
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
cuguauguug guagccacgc                                              20

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 10
ucuguguggg auguggccc                                                  19

<210> SEQ ID NO 11
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
auguauguug ggagccacgc                                                 20

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ucuguugugc uugauaugcc c                                               21

<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
ugguguguca agguacgcgc                                                 20

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ucugcugugc uugauaugcc c                                               21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ucuguugugc uugauaugcc c                                               21

<210> SEQ ID NO 16
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 16
cugucuaccu ucuacugccg                                               20

<210> SEQ ID NO 17
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
ccaguuuacc uuacacucgc                                               20

<210> SEQ ID NO 18
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
cgaugcuuac gugcacgcgc                                               20

<210> SEQ ID NO 19
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
cugucuaccu ucuacugccc                                               20

<210> SEQ ID NO 20
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uugucuaccu ucuacugccg                                               20

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
cugucuwmgc uucuacugcc g                                             21

<210> SEQ ID NO 22
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 22
uccugucguc uguucguccc                                              20

<210> SEQ ID NO 23
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ccgugucguc uguacugccc                                              20

<210> SEQ ID NO 24
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
uccugucguy ugkucskccc                                              20

<210> SEQ ID NO 25
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
gggaggacga ugcgggacug uaygggcuc ugugcagacg acucgcccga               50

<210> SEQ ID NO 26
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
gggaggacga ugcggucugu ugugcuugau augccccaga cgacucgccc ga           52

<210> SEQ ID NO 27
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
gggaggacga ugcggcuguc uwmgcuucua cugccgcaga cgacucgccc ga           52

<210> SEQ ID NO 28
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 28
gggaggacga ugcggaugua uguugggagc cacgccagac gacucgcccg a         51

<210> SEQ ID NO 29
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gggaggacga ugcgguccug ucguyugkuc skccccagac gacucgcccg a         51

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
gcugucacag aggggcuacu u                                          21

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
guagccccuc ugugacagcu u                                          21

<210> SEQ ID NO 32
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
gggaggacga augcgggacu guacggggcu cugugcagac gacucgcccg agcugucaca    60
gaggggcuac uu                                                       72

<210> SEQ ID NO 33
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
gggaggacga ugcgggacug uaugggcuc ugugcagacg acucgcccga gcugucacag     60
aggggcuacu u                                                        71

<210> SEQ ID NO 34
<211> LENGTH: 70
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 34 ggggaggacga ugcgggacug uacgggcucu gugcagacga cucgcccgag cugucacaga    60
ggggcuacuu                                                           70

<210> SEQ ID NO 35
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35 ggggaggacga ugcggucugu gugcuugau augccccaga cgacucgccc gagcugucac    60
agaggggcua cuu                                                       73

<210> SEQ ID NO 36
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36 ggggaggacga ugcgguggug ugucaaggua cgcgccagac gacucgcccg agcugucaca   60 gagggcuac uu                                                         72

<210> SEQ ID NO 37
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37 ggggaggacga ugcggucugc ugugcuugau augccccaga cgacucgccc gagcugucac   60
agaggggcua cuu                                                       73

<210> SEQ ID NO 38
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38 ggggaggacga ugcggcuguc uaccuucuac ugccgcagac gacucgcccg agcugucaca   60 gagggcuac uu                                                         72

<210> SEQ ID NO 39
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 39
gggaggacga ugcggcgaug cuuacgugca cgcgccagac gaacucgccc gagcugucac    60
agaggggcua cuu                                                      73

<210> SEQ ID NO 40
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
gggaggacga ugcggcgaug cuuacgugca cgcgccagac gacucgcccg agcugucaca    60
gaggggcuac uu                                                       72

<210> SEQ ID NO 41
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
gggaggacga ugcggaugua uguugggagc cacgccagac gacucgcccg agcugucaca    60
gaggggcuac uu                                                       72

<210> SEQ ID NO 42
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
gggaggacga ugcggcugua uguugguagc cacgccagac gacucgcccg agcugucaca    60
gaggggcuac uu                                                       72

<210> SEQ ID NO 43
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
gggaggacga ugcggucugu gugggaugug gccccagacg acucgcccga gcugucacag    60
aggggcuacu u                                                        71

<210> SEQ ID NO 44
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 44
gggaggacga ugcgguccug ucgucuguuc gucccagacg acucgcccga gcugucacag    60
aggggcuacu u                                                        71

<210> SEQ ID NO 45
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(36)
<223> OTHER INFORMATION: a, c, u, g, unknown or other and this region
      may encompass 19 to 21 nucleotides

<400> SEQUENCE: 45
gggaggacga ugcggnnnnn nnnnnnnnnn nnnnnncaga cgacucgccc ga            52
```